(12) United States Patent
Almog et al.

(10) Patent No.: US 8,523,755 B2
(45) Date of Patent: Sep. 3, 2013

(54) VENTRICULAR FUNCTION ASSISTING DEVICES AND METHODS OF USE THEREOF

(75) Inventors: Remo Eyal Almog, Tel-Aviv (IL); Amit Tubishevitz, Tel-Aviv (IL)

(73) Assignee: Corassist Cardiovascular Ltd., Herzlia (IL)

( * ) Notice: Subject to any disclaimer, the term of this patent is extended or adjusted under 35 U.S.C. 154(b) by 227 days.

(21) Appl. No.: 12/805,656

(22) Filed: Aug. 11, 2010

(65) Prior Publication Data

US 2011/0092761 A1    Apr. 21, 2011

Related U.S. Application Data

(63) Continuation-in-part of application No. PCT/IL2009/000159, filed on Feb. 11, 2009.

(60) Provisional application No. 61/027,495, filed on Feb. 11, 2008.

(51) Int. Cl.
*A61N 1/362* (2006.01)

(52) U.S. Cl.
USPC .............................................. 600/16; 600/37

(58) Field of Classification Search
USPC .......................................... 600/16, 37; 607/9
See application file for complete search history.

(56) References Cited

U.S. PATENT DOCUMENTS

| | | | | |
|---|---|---|---|---|
| 5,702,343 | A * | 12/1997 | Alferness ........................ | 600/37 |
| 6,375,609 | B1 | 4/2002 | Hastings et al. | |
| 6,425,856 | B1 * | 7/2002 | Shapland et al. ............... | 600/37 |
| 7,146,226 | B2 * | 12/2006 | Lau et al. ....................... | 607/129 |
| 2003/0060674 | A1 | 3/2003 | Gifford | |
| 2004/0143154 | A1 | 7/2004 | Lau et al. | |
| 2006/0009675 | A1 | 1/2006 | Meyer | |
| 2007/0106359 | A1 | 5/2007 | Schaer | |
| 2008/0071134 | A1 * | 3/2008 | Dubi et al. ...................... | 600/16 |
| 2009/0187064 | A1 * | 7/2009 | Abrams .......................... | 600/16 |
| 2011/0092761 | A1 * | 4/2011 | Almog et al. ................... | 600/16 |

FOREIGN PATENT DOCUMENTS

| | | |
|---|---|---|
| DE | 199 33 522 | 9/2000 |
| EP | 1 258 259 | 11/2002 |
| WO | WO 00/78376 | 12/2000 |
| WO | WO 2004/066805 | 8/2004 |
| WO | WO 2005/102181 | 11/2005 |
| WO | WO 2008/038276 | 4/2008 |

OTHER PUBLICATIONS

International Search Report for PCT/IL2009/000159, mailed Nov. 16, 2009.
Written Opinion of the International Searching Authority for PCT/IL2009/000159, mailed Nov. 16, 2009.

* cited by examiner

*Primary Examiner* — Joseph Stoklosa
(74) *Attorney, Agent, or Firm* — Nixon & Vanderhye P.C.

(57) ABSTRACT

Devices and methods are provided for assisting in the ventricular function of a treated heart, and tools for delivering and attaching elements of said devices to the wall of the heart. In general the devices are designed to assist in the ventricular function of the heart by utilizing elastic, and/or magnetic, elements designed to apply radially and/or tangentially directed forces over the wall of the heart, and/or alter the pressure conditions inside ventricle(s) of the heart. Embodiments may utilize restrictive elements which may optionally be attached over the heart during the implantation procedure, or at a later time, by changing the mode of operation of an implanted device.

16 Claims, 17 Drawing Sheets

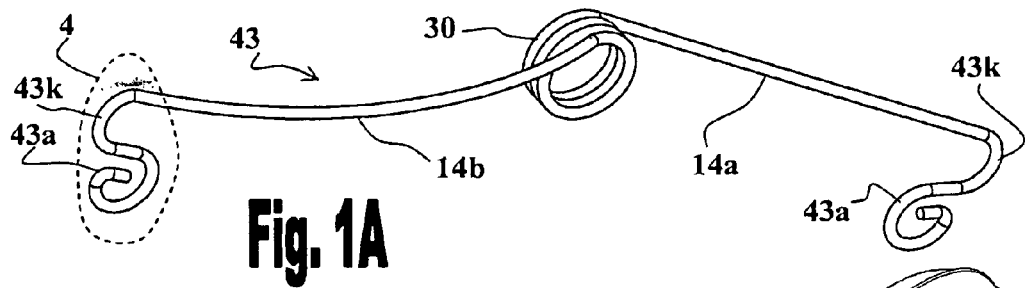
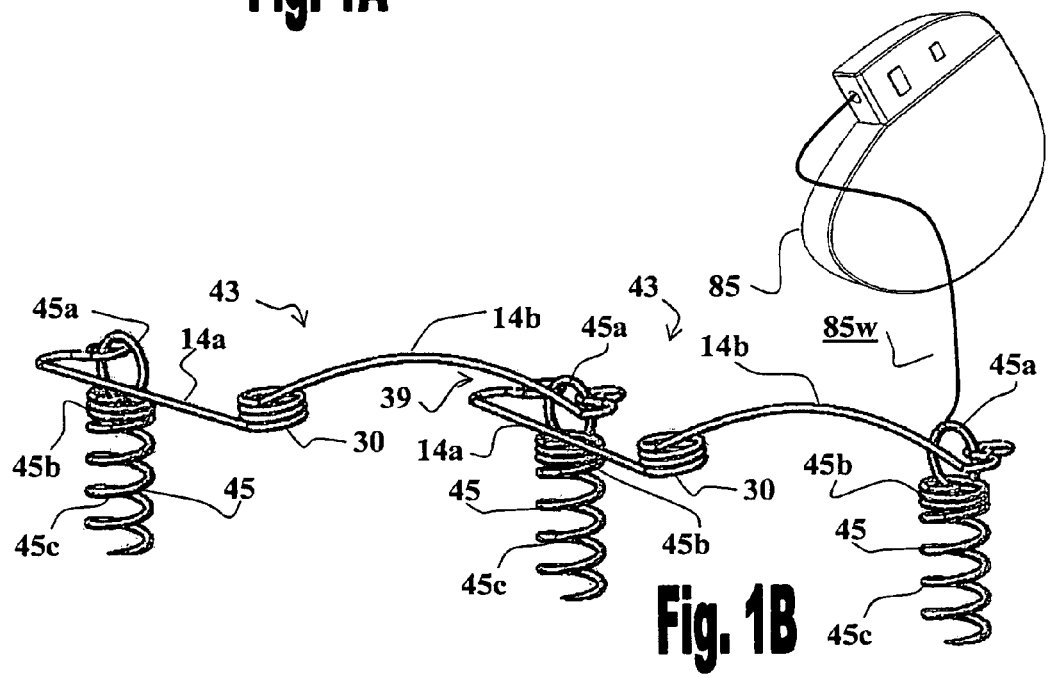
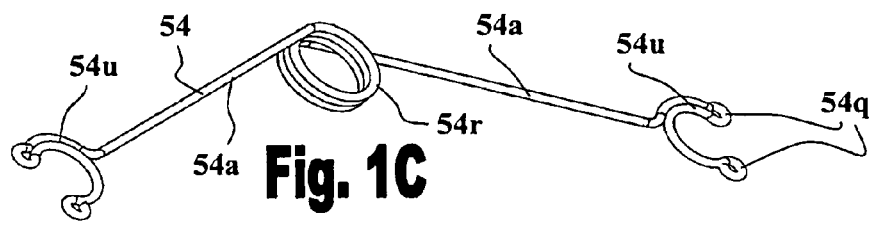

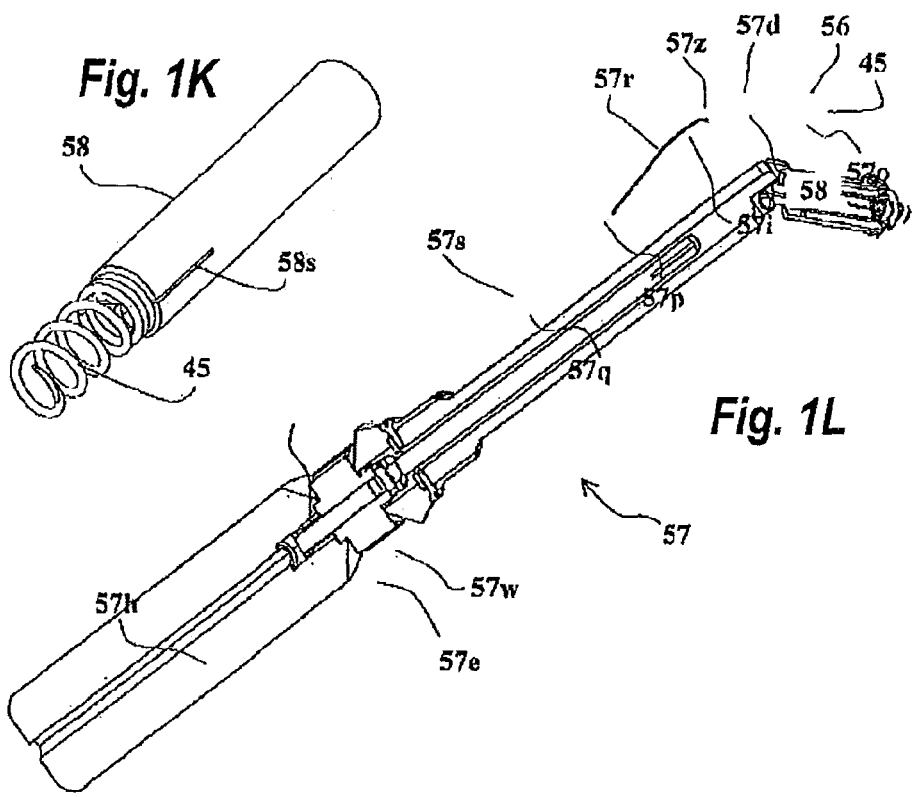
Fig. 1K
Fig. 1L
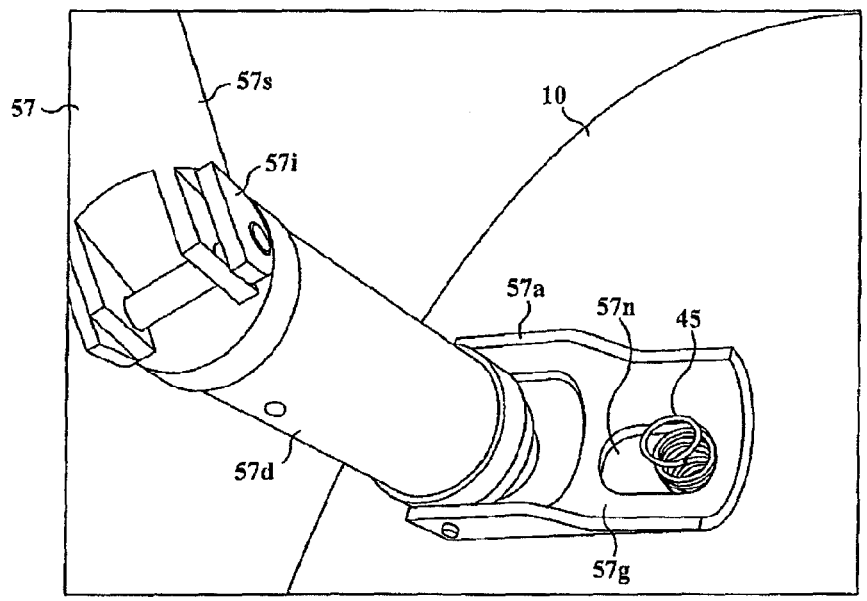
Fig. 1M

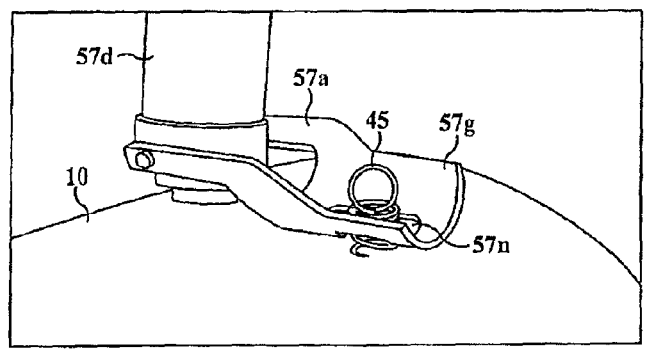
Fig. 1N
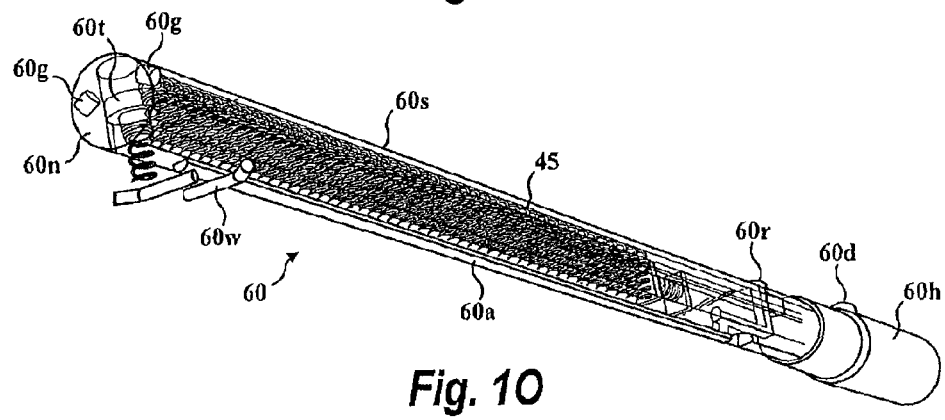
Fig. 1O
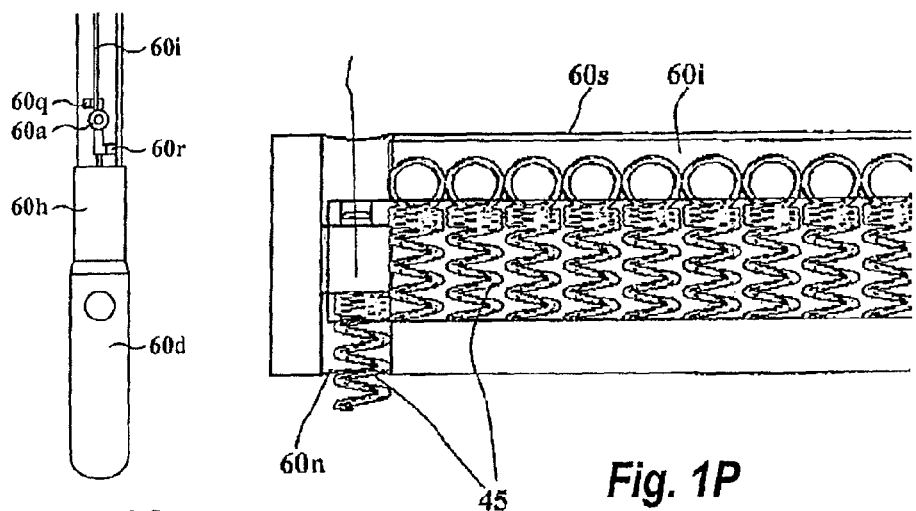
Fig. 1Q
Fig. 1P

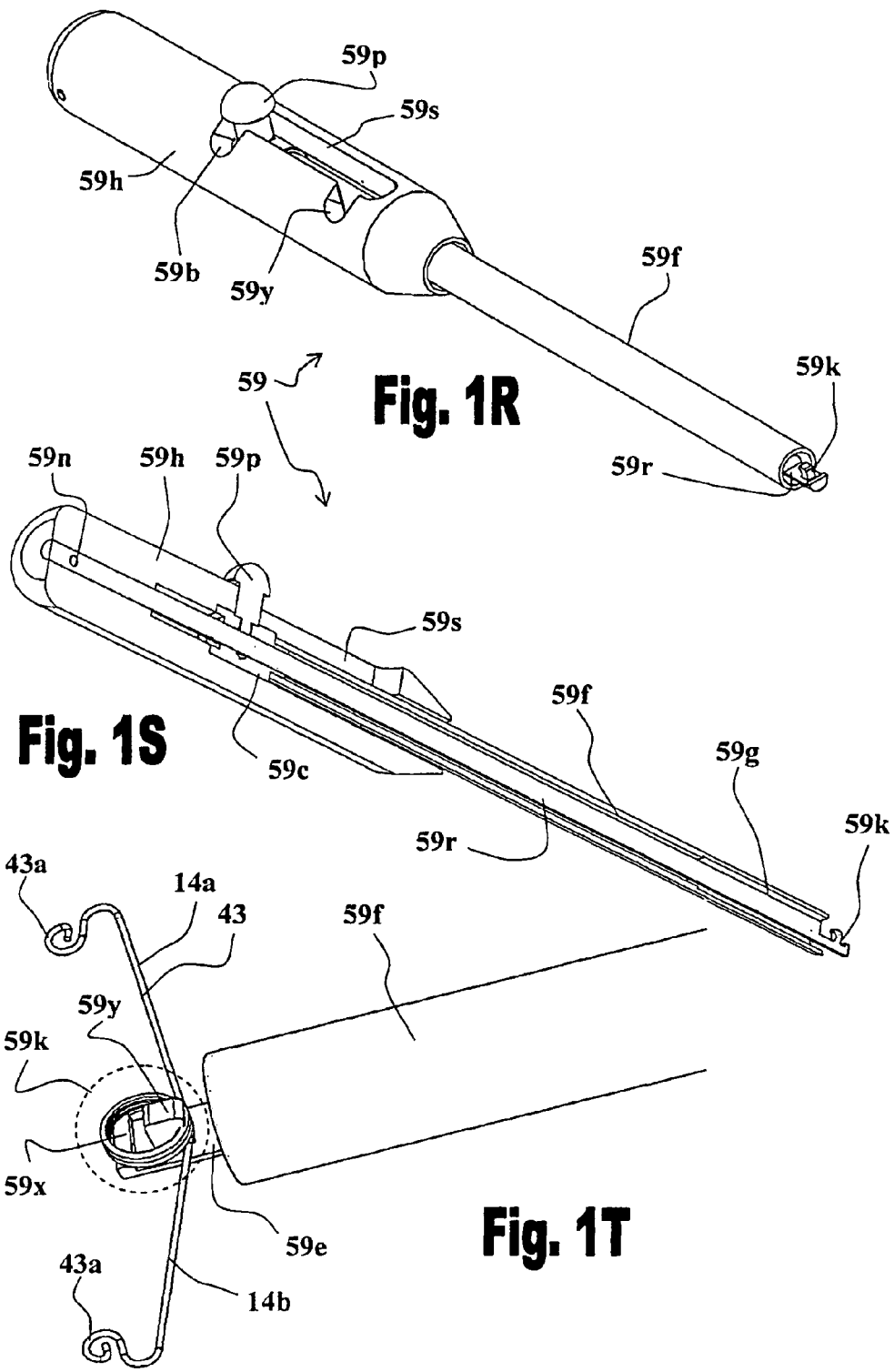

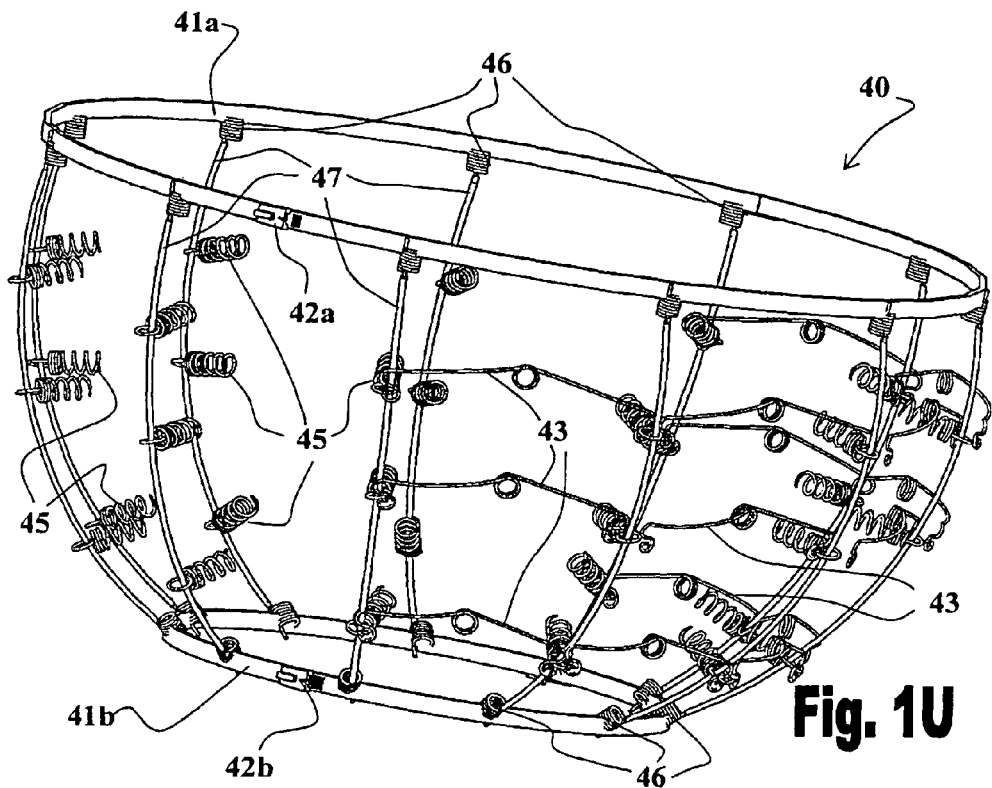
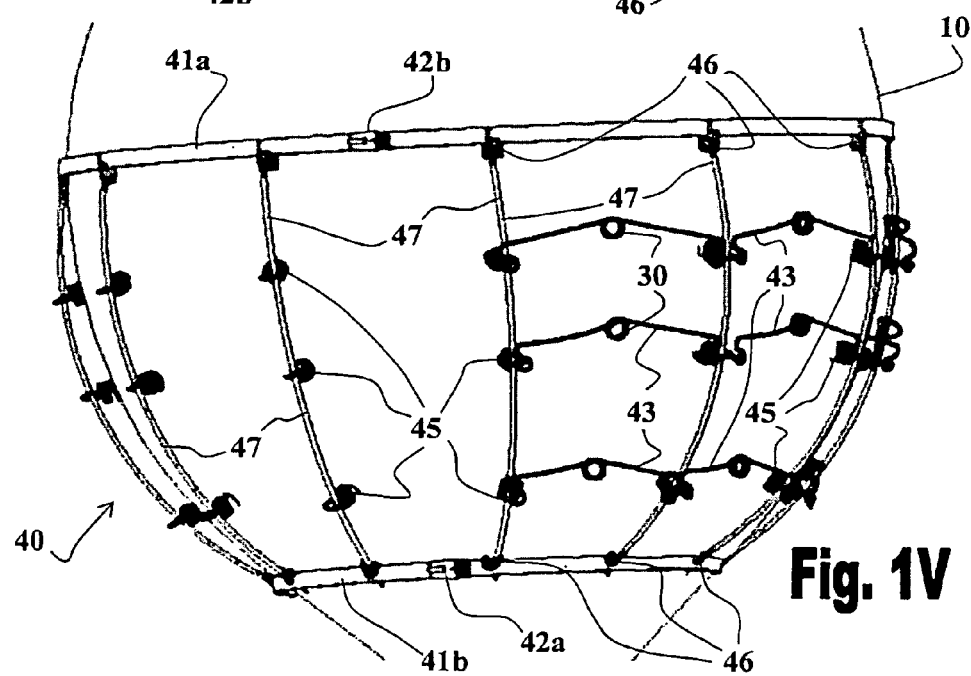

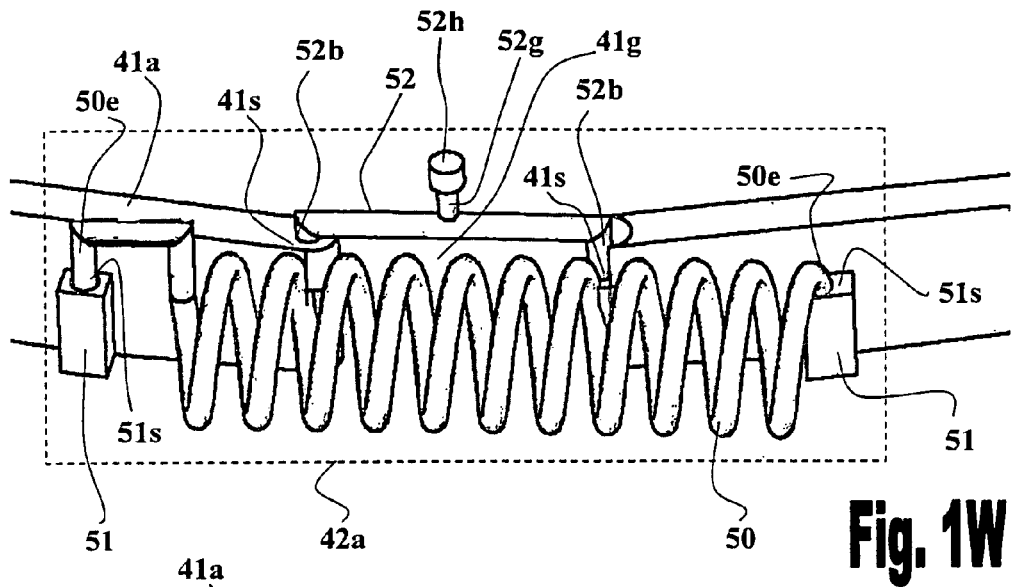
Fig. 1W
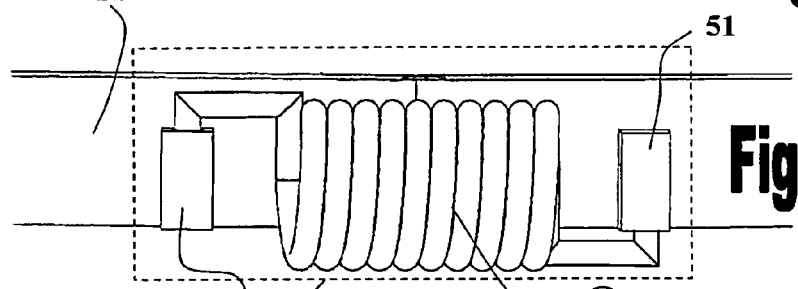
Fig. 1X
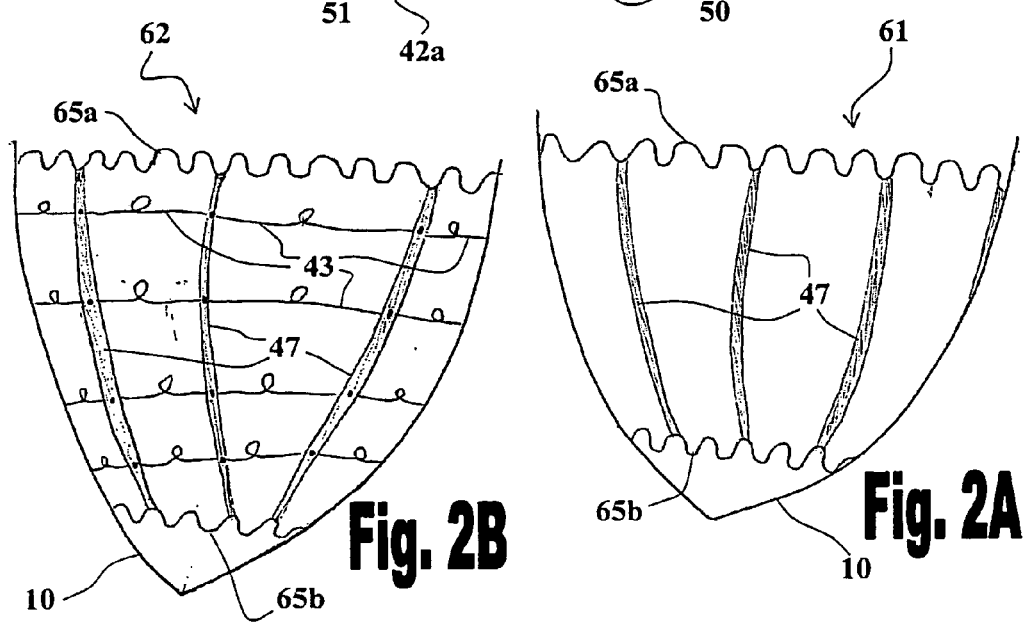
Fig. 2B   Fig. 2A

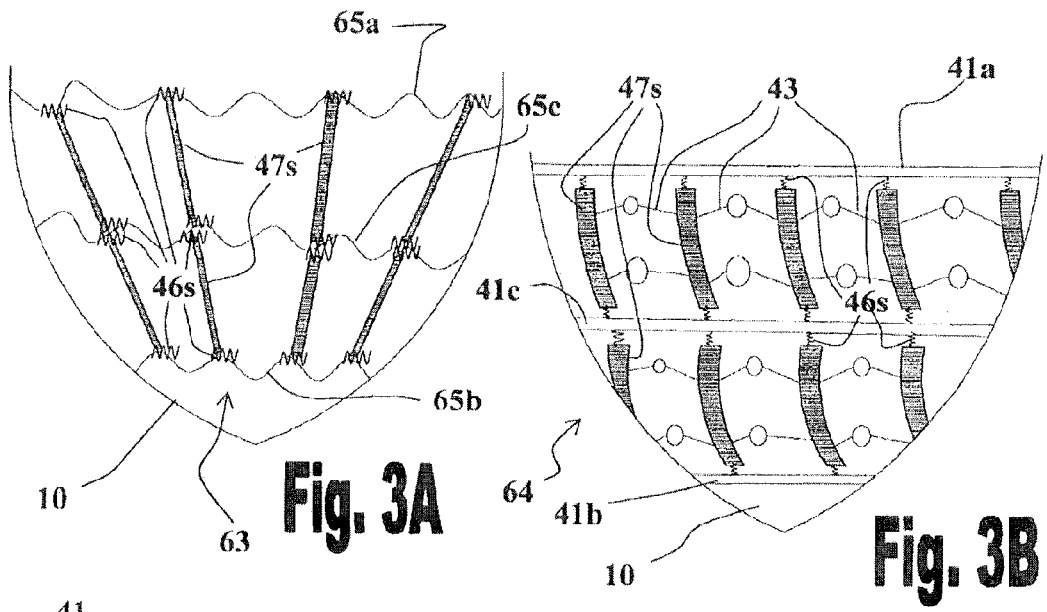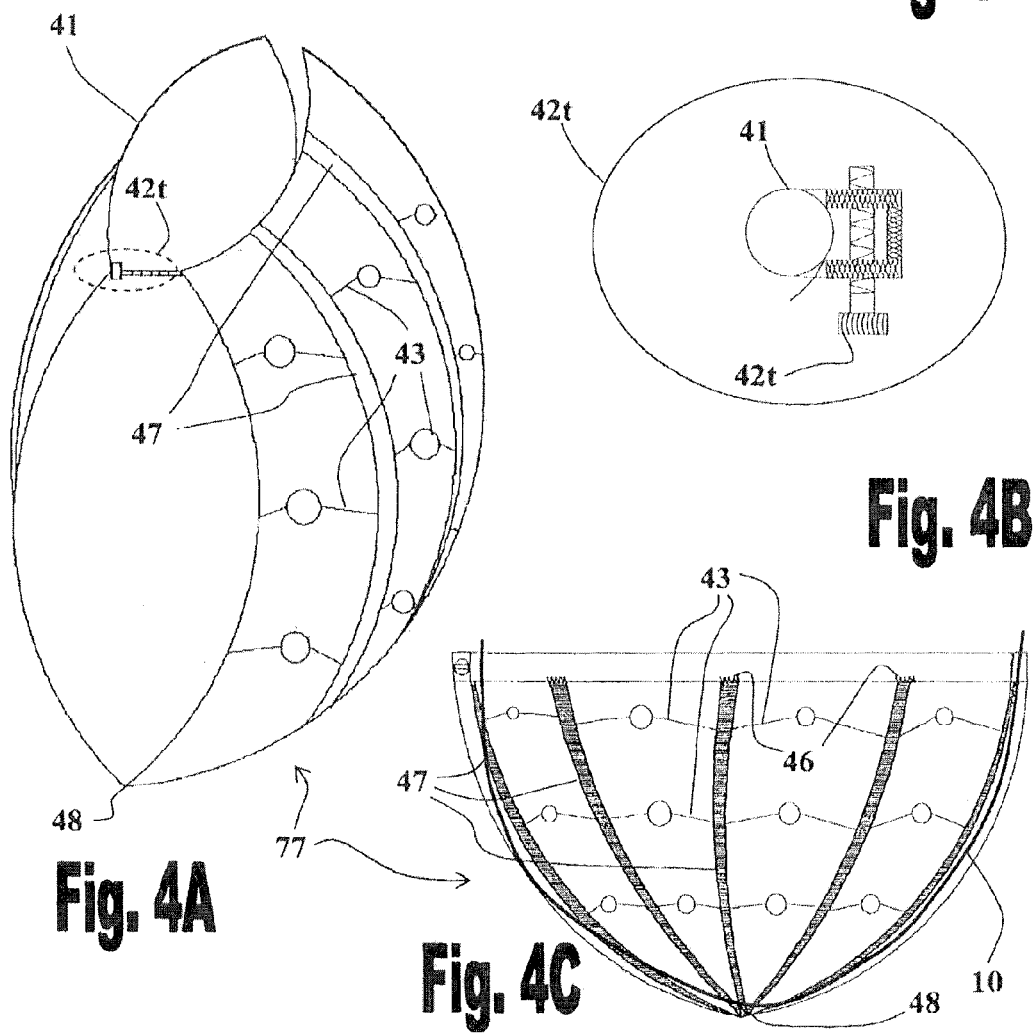

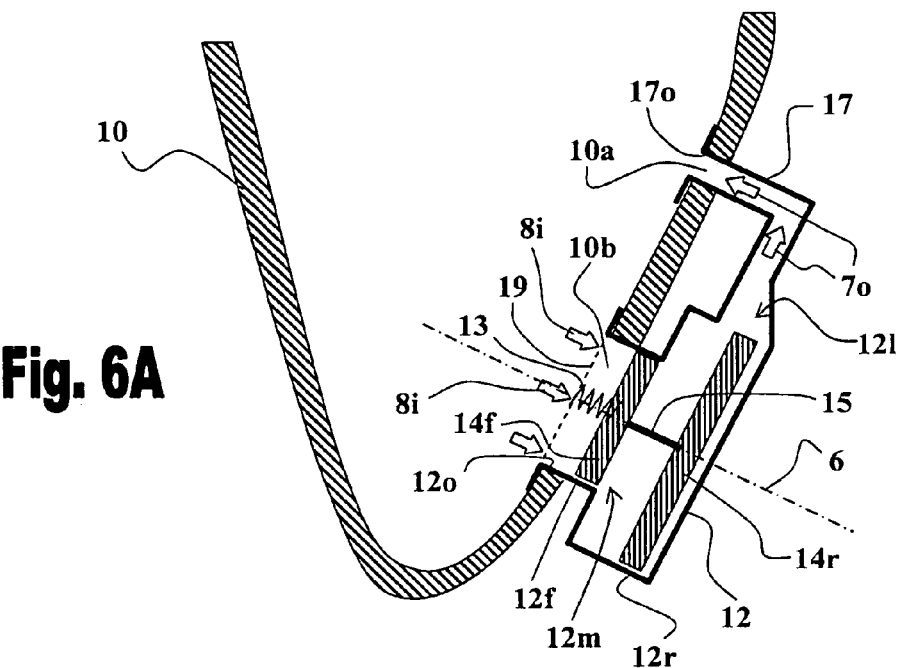
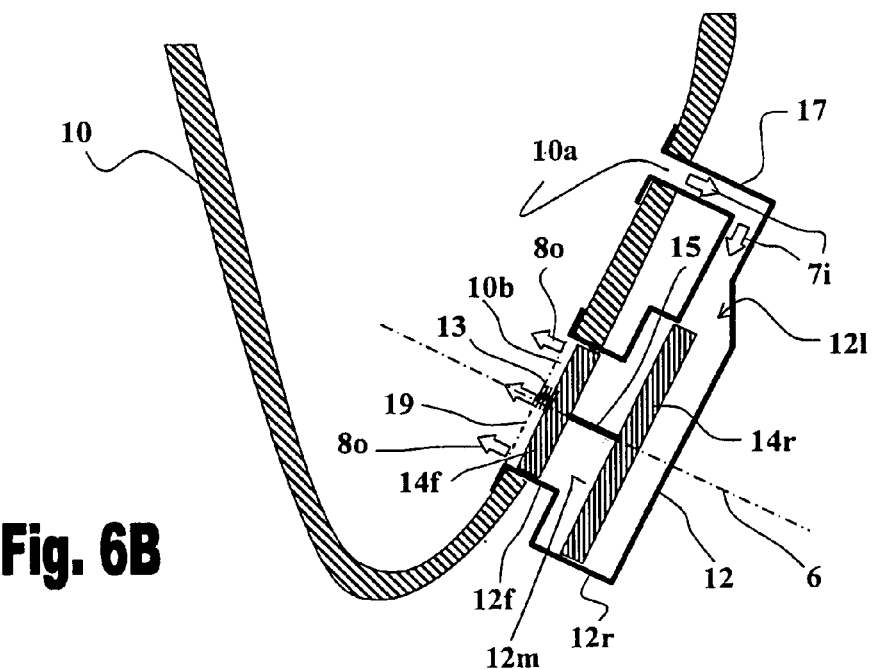

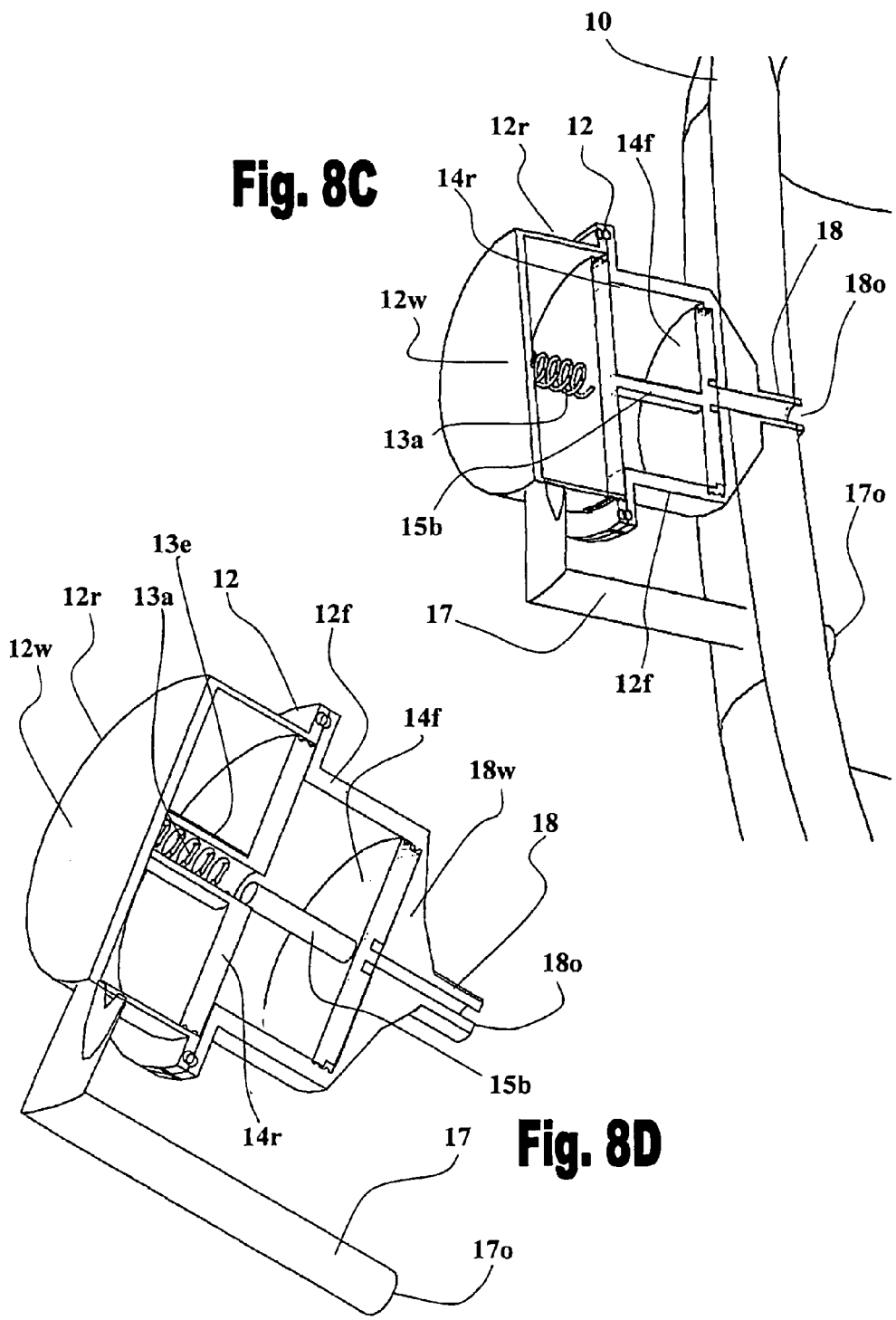

VENTRICULAR FUNCTION ASSISTING DEVICES AND METHODS OF USE THEREOF

This application is a Continuation-In-Part of International Application No. PCT/IL2009/000159, filed 11 Feb. 2009, which designated the U.S. and claims the benefit of U.S. Provisional Application No. 61/027,495, filed 11 Feb. 2008, the entire contents of which is hereby incorporated by reference.

FIELD OF THE INVENTION

The present invention relates to methods and devices for improving ventricular function of the heart. More particularly, the invention relates to means for treating systolic and/or diastolic heart dysfunctions.

BACKGROUND OF THE INVENTION

Heart failure (HF) is a complex clinical syndrome that can result from any structural or functional cardiac disorder that impairs the ability of the ventricle to fill with or eject blood. The cardinal manifestations of HF are dyspnea and fatigue, which may limit exercise tolerance, and fluid retention, which may lead to pulmonary congestion and peripheral edema. Heart failure is most commonly associated with impaired left ventricle (LV) systolic function.

The term diastolic heart failure (DHF) generally refers to the clinical syndrome of heart failure associated with preserved left ventricular ejection fraction, in the absence of major valvular disease.

Primary diastolic dysfunction is typically observed in patients with hypertension and hypertrophic or restrictive cardiomyopathy, but can also occur in a variety of other clinical disorders and has a particularly high prevalence in the elderly population. Aging is associated with 'physiologic' diastolic dysfunction due to the increase in LV muscle mass and changes in passive elastic properties of the myocardium, hence, the concern of an increase in the incidence of diastolic dysfunction as the aging of the western world population progresses.

There is thus a need for, and it would be highly advantageous to have an in-vivo method and device for improving diastolic function of the heart, while minimally disturbing systolic function of the heart. Moreover, there is a need for such a method and device which is biocompatible and is specially configured for compact and long-term reliable use in humans.

Various in-vivo methods and devices for improving diastolic function of the heart are described in International patent applications Nos. PCT/IL02/00547 (WO 03/007778), PCT/IL05/01014 (WO 06/033107), PCT/IL04/00986 (WO 05/041745), and PCT/IL04/00072 (WO 04/066805), of the same assignee hereof, the descriptions of which is incorporated herein by reference. The aforementioned international patent applications describe elastic means used for improving diastolic function of the right or left ventricle of the heart by pushing and/or pulling, an inner and/or outer wall region of the ventricle during the cardiac cycle while minimally disturbing the heart function. The present invention provides modifications, improvements, and new methods and devices, for improving the diastolic function of the heart.

SUMMARY OF INVENTION

The present invention provides devices and methods for assisting in the ventricular function of a treated heart, and tools for delivering and attaching elements of said devices to the wall of the heart. In general the devices of the invention are designed to assist in the ventricular function of the heart by utilizing elastic, and/or magnetic, elements designed to apply radially and/or tangentially directed forces over the wall of the heart, and/or alter the pressure conditions inside ventricle(s) of the heart.

Embodiments of the invention further utilize restrictive elements which may optionally be attached over the heart during the implantation procedure, or at a later time, by changing the mode of operation of an implanted device of the invention.

In one aspect the present invention is directed to an apparatus capable of selectively assisting diastolic dysfunctions and/or systolic dysfunctions by means of elastic or magnetic elements attached to the wall of the heart and configured to apply radially and/or tangentially directed forces thereover. Said apparatus further comprises restrictive elements adapted to encircle a perimeter (circumference) of the heart and capable of being changed between an engaging state and a non-engaging state, where in said engaging state they restrict heart expansions during the diastolic phase and in said non-engaging state the diastolic phase is not affected by them.

According to one preferred embodiment of the invention the ventricular function assisting apparatus comprises anchoring means capable of being attached to the wall of the heart, elastic elements capable of being attached to said anchoring means, at least two restrictive elements adapted to encircle a perimeter of the heart, said restrictive elements capable of being changed between a engaging state and a non-engaging state over the heart, and elongated flexible elements capable of being attached between said restrictive elements via their extremities while being movably engaged in said anchoring means along portions of their lengths, wherein said ventricular function assisting device is capable of being selectively changed between two modes of operation by changing the state of said restrictive means between their non-engaging and engaging states over the heart.

The ventricular function assisting device of the invention is preferably attached over the heart by placing at least two restrictive elements more or less horizontally around the heart, attaching the anchoring means to wall region(s) of the heart located between the restrictive elements, attaching the elastic elements to said anchoring means such that they can be elastically deformed and store potential energy in them during the systolic phase and release said stored energy during the diastolic phase, thereby applying radially outward and tangentially directed forces over said wall regions, and attaching the extremities of said elongated flexible elements between said restrictive elements such that at least some of them are movably engaged in said anchoring means.

The elastic elements are generally made in a "v" like shape having torsion loop(s) at its apex and two arms attached by one of their ends to said torsion loops, where each of said side arms comprising attachment components at their other end. Preferably, the elastic elements are made from an elastic wire coiled into a "V" like shape such that torsion loop(s) are formed at its apex with two side arms, wherein the end portions of said side arms are curved to form the attachment components. According to one specific embodiment the attachment components are made in a "G"-like shape. In an alternative embodiment the attachment components are made in a "U"-like shape.

The anchoring means are preferably made from a turned wire having a bottom and top portions, wherein said bottom portion is formed in a helical shape adapted to be screwed into a soft tissue and its top portion comprises one or more retaining parts configured to receive the attachment components provided in the elastic elements, wherein some, or all, of the retaining parts are further adapted to movably hold a potion of the elongated flexible elements. In a preferred embodiment of the invention the retaining parts are made from a curved wire configured to receive and hold the attachment components of the elastic elements while allowing non-interlocking passage of the elongated flexible elements through it. Most preferably, the retaining part is formed in a shape of a vertical ring being in a plane substantially vertical to the plane of the helical turns of the bottom portion of the anchoring means. The top portion of the anchoring means may be implemented by a flanged rod having circumferential gaps formed between its flanges used as retaining parts suitable to receive and hold the attachment components of the elastic elements. The top portions of the anchoring means may further comprise a dome-like cover for preventing tissue injuries.

The restrictive elements are preferably made from a rigid, or semi-rigid, circular stripe having a fastening mechanisms capable of changing its circumference from a non-engaging state into it engaging state by reducing its circumference. The fastening mechanism may be implemented by a fastening screw (e.g., as a gear clamp). Alternatively, the fastening mechanism may be implemented by a spring and a removable support bar attached over a gap formed in the restrictive element configured such that its circumference may be reduced by removing said removable support bar.

According to one embodiment the restrictive elements have a wavy configuration or implemented by tension springs. Advantageously, the flexible elongated elements may attached to the restrictive elements by means pulling, or pushing, springs.

In another specific embodiment the flexible elongated elements are attached at one end to a restrictive element while their other end is are attached together by a connecting component near the apex of the heart.

Advantageously, the elastic elements are attached to anchoring means placed over the left ventricle of the heart, such that when the restrictive elements of the ventricular function assisting device are in their non-engaging state the apparatus substantially assists in diastolic heart dysfunction, and whenever said restrictive elements are changed into their engaging state the apparatus substantially assists in both diastolic and systolic heart dysfunctions.

In another aspect the present invention is directed to a kit comprising the elements of ventricular function assisting device of the invention and tools capable of delivering and attaching the anchoring means to the heart, and tools capable of delivering and attaching the elastic elements to said anchoring means, wherein said tools are capable of delivering and attaching said elements and means via a minimally invasive procedure.

According to one embodiment the kit comprises fastening means capable of holding the top portion of the anchoring means, and a screwing tool comprising: a proximal handle having a rotatable wheel disposed in its; a hollow shaft attached to said handle, said hollow shaft comprises a rotatable rod mechanically linked to said rotatable wheel; a hinged head attached at the distal end of said hollow shaft in which there is a rotatable holder capable of receiving and holding said fastening means in it, wherein said rotatable rod and said rotatable holder are mechanically linked such rotations of said wheel are delivered thereby to said rotatable holder. The hinged head may further comprise foldable locator capable of indicating the distance between adjacent anchoring means place on the wall of the heart.

Additionally or alternatively, the kit may comprise a delivery tool having an elongated stack capable of holding a plurality of anchoring means, said elongated stack comprising a pushing spring adapted to advance the anchoring means distally toward a distal opening wherein there is a screwing head mechanically linked to an electrical motor and capable of holding the distal-most anchoring means in said stack and move it out of said stack via said distal opening. Advantageously, the delivery tool may further comprise optical guiding means mounted on opposing sides in a distal section thereof which are adapted to emit a light beam capable of designating a new location for placing a new anchoring means.

The kit may further comprise a delivery tool suitable for delivering and attaching the elastic elements, comprising a proximal handle having a slider element movably placed therein and capable of being moved between a proximal and distal states, a slidable hollow shaft comprising mechanically linked to said slider element, and a an elongated rod fixedly attached to said proximal handle and passing inside said handle and said slidable hollow shaft, wherein said elongated rod comprises a retaining part adapted to receive and hold the torsion loop(s) of an elastic element when said slider element in its proximal state, such that the arms of said elastic elements are capable of being folded into said slidable hollow shaft by changing the state of said slider element into its distal state.

In another aspect the present invention is directed to a ventricular function assisting device utilizing a plunger mechanism designed to increase the volume of the left ventricle of the heart during diastolic phase and reduce its volume during the systolic phase.

According to one preferred embodiment the ventricular function assisting device comprises a cylindrical housing having a front section having a front opening capable of being sealably attached to a first opening formed in a ventricle of the heart, and a rear section to which there is attached a conduit capable of communicating between said rear section and said ventricle via a second opening formed therein to which said conduit is capable of being sealably attached, wherein each of said sections comprises a slidable plunger movably disposed thereinside, said plungers are mechanically linked by a connecting rod, and wherein the cross-sectional area of the plunger in the rear section is greater than the cross-sectional area of the plunger in the front section, and wherein said plungers are mechanically linked to an elastic element (e.g., spring) mounted inside said ventricular function assisting device and adapted to push, or pull said plungers thereinside.

According to another preferred embodiment the ventricular function assisting device comprises a cylindrical housing a slidable plunger slibably disposed thereinside, said slidable plunger is made from a magnetic or ferromagnetic material, a front and rear coils wound on, or in, the wall of said cylindrical hosing, and a front opening, or passage, capable of being attached to an opening formed in a ventricle of the heart and communicating between said cylindrical housing and said ventricle, wherein said coils are capable of being electrically connected to a controllable current source configured to activate said coils, or one of them, to apply magnetic forces for sliding said slidable plunger rearwardly during the diastole, and to apply magnetic forces for sliding said slidable plunger forwardly during the systole.

BRIEF DESCRIPTION OF THE DRAWINGS

The present invention is illustrated by way of example in the accompanying drawings, in which similar references consistently indicate similar elements and in which:

FIGS. 1A to 1X schematically illustrate various embodiments of ventricular function assisting devices configured for treating systolic and diastolic dysfunctions and tools suitable for attaching the same to the heart in a minimally invasive procedure, wherein FIGS. 1A and 1B show a configuration of anchoring means and elastic elements having G-shaped attachments suitable for use in the ventricular function assisting device, FIGS. 1C to 1F show embodiments of anchoring means having dual-level anchoring sites in their head sections and elastic elements having C-shaped attachments, FIGS. 1O to 1Q show another embodiment of a tool for attaching the attachment means to the wall of the heart in which the attachment means are maintained in an internal stack, FIGS. 1R to 1T shows a tool for delivering and attaching the elastic elements, FIG. 1U shows a perspective view of the ventricular function assisting device of the invention having two operation modes, FIG. 1V shows the ventricular function assisting device shown in FIG. 1U when mounted on a heart, and FIGS. 1W and 1X illustrate an exemplary implementation of a fastening mechanism (in an open and closed states, respectively) suitable for fastening the ventricular function assisting device over the heart;

FIGS. 2A and 2B schematically illustrate a ventricular function assisting device which employs elastic restrictive elements;

FIGS. 3A and 3B schematically illustrate ventricular function assisting devices for treating systolic and diastolic dysfunctions which employ an intermediate restrictive element;

FIGS. 4A to 4C schematically illustrate an implementation of the ventricular function assisting device which is configured to enclose the apex of the heart, wherein FIG. 4A is a perspective view, FIG. 4B schematically illustrates an exemplary fastening mechanism, and FIG. 4C is a side view;

FIGS. 6A and 6B schematically illustrate the structure and operation of a ventricular function assisting device of the invention based on an plunger mechanism;

FIGS. 8A to 8E show sectional views of various implementations of ventricular function assisting devices of the invention based on plunger mechanisms, wherein FIG. 8A shows an embodiment employing an anterior spring, FIG. 8B shows an embodiment employing a posterior spring, FIG. 8C exemplifies attachment of an embodiment employing a posterior spring to the heart, FIG. 8D shows an embodiment employing a posterior spring placed in an isolating enclosure, and FIG. 8E exemplifies attachment of an embodiment employing an anterior spring to the heart;

Figure 1D:
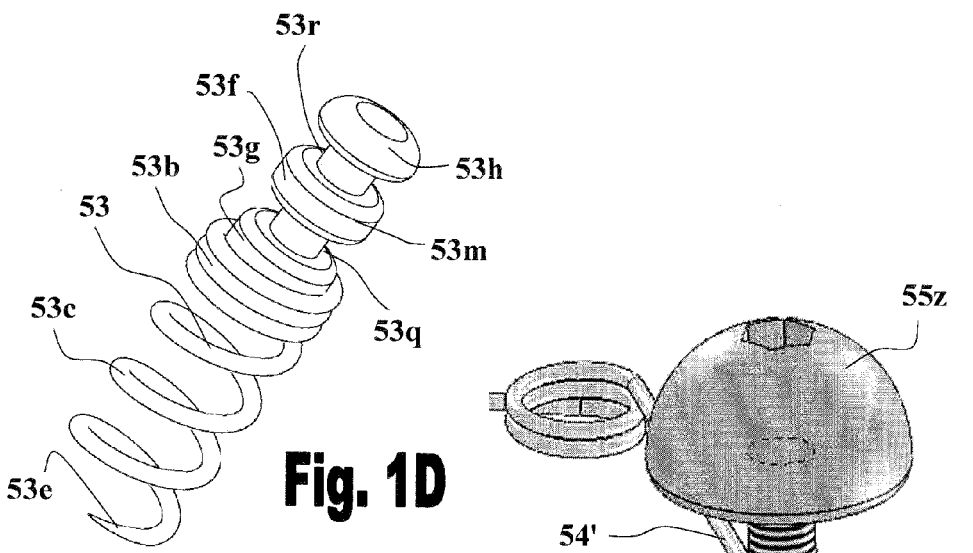

It should be noted that the embodiments exemplified in the Figs. are not intended to be in scale and are in diagram form to facilitate ease of understanding and description.

DETAILED DESCRIPTION OF PREFERRED EMBODIMENTS

The present invention provides methods and devices for treating systolic and/or diastolic heart dysfunctions and delivery tools suitable for delivering and attaching elements to the wall of the heart in a minimally invasive procedure. In general, devices of the present invention are designed to assist the operation of the heart by aiding in volume enlargement of the left ventricle and by reducing the pressures thereinside during diastolic function, and aiding in the pumping of blood from the left ventricle during systolic function. Some embodiments of the invention are further configured to limit ventricular dilatation in the treatment of systolic dysfunctions, wherein the limiting of ventricular dilatation may be activated at a later time after installing the device on a patient's heart (also referred to herein as devices having two operation modes).

In one preferred embodiment of the invention the ventricular function assisting device is composed of elastic elements designed to be attached to the wall of the left ventricle, and of restrictive elements (e.g., rings or stripes) designed to be fastened over the heart of the patient. FIGS. 1A to 1X illustrate various preferred embodiments of a ventricular function assisting devices comprising elastic (or resilient) elements (43 or 54) having "V"-like shape (e.g., torsion springs), and in some embodiment also restrictive elements, 41a and 41b (shown in FIGS. 1U and 1V), and tools that may be used for assisting in the attachment of these elements.

In this preferred embodiment ventricular function assisting device (40 shown in FIGS. 1U and 1V) is designed to operate in two different modes. In the first mode of operation, device is attached to the patient's heart such that elastic elements 43 attached over the left ventricle apply tangential and radial forces thereover during contractions and expansions thereof, while the restrictive elements, 41a and 41b, are in a non-operative state, namely, said restrictive elements 41a and 41b are placed around the patient's heart (10) such they do not interfere with its expansions.

The first mode of operation of device 40 is mainly directed for treating diastolic dysfunctions. During the systole elastic elements 43 are compressed (the distance between their arms is reduced) as they store elastic potential energy. During diastole, the elastic potential energy stored in elastic elements 43 is released as they apply radial and tangential forces over their respective attachment elements 45.

In the second mode of operation of device 40 the perimeter of restrictive elements 41 is diminished by means of a fastening mechanism 42 (42a in upper restrictive element 41a and 42b in lower restrictive element 41b) such that said restrictive elements 41a and 41b and the patient's heart become engaged. The second mode of operation of device 40 is mainly directed for treating systolic dysfunctions. As will be explained hereinbelow the mode of operation of device 40 may be changed from the first mode to the second mode at a later time, after installing the device. This configuration is particularly desirable in patients initially suffering from diastolic dysfunctions and which develop systolic dysfunction ailments during later treatment stages.

FIGS. 1A and 1B show a configuration of anchoring means 45 and elastic elements 43 suitable for use in the ventricular functions assisting device 40 (shown in FIGS. 1U and 1V). Elastic element 43 is preferably a type of torsion spring made from an elastic wire formed in a "V"-like shape, having torsion loop(s) 30 at its apex and "G"-shaped anchoring loops 43a at the end of its arms. Anchoring loops 43a may have a spiral shape and they are preferably formed by bending the end sections of the arms towards spring loop(s) 30, thereby forming knees 43k, and thereafter bending said end sections away from said spring loop(s) 30 to form a spiral shape therewith. In this way an "S"-like shape (marked by dotted line 4 in FIG. 1A) is formed at the end of each arm, wherein the bottom portion of the "S"-like shape is further curved to form the "G"-shaped curved fasteners 43a.

As best seen in FIG. 1A, elastic element 43 comprises a first arm 14a which is relatively straight, and a second arm 14b which is curved relative to the plain of the element. As shown in FIG. 1B, in the attachment of elastic elements 43 to attachment elements 45, second arms 14b of elastic elements 43 are curved such that the straight arm 14a of the adjacent elastic element may be passed beneath the curved arm to engage the head section of the attachment element 45 while maintaining a gap 39 therebetween.

Figure 1E:
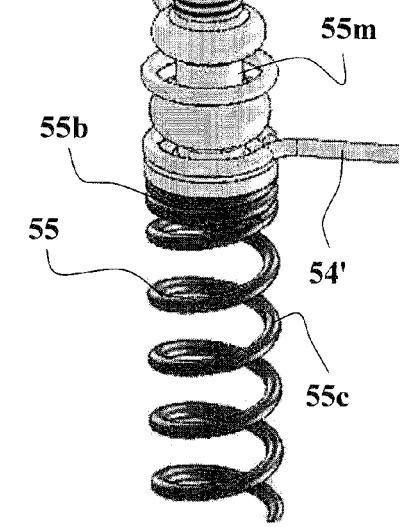
Figure 1F:
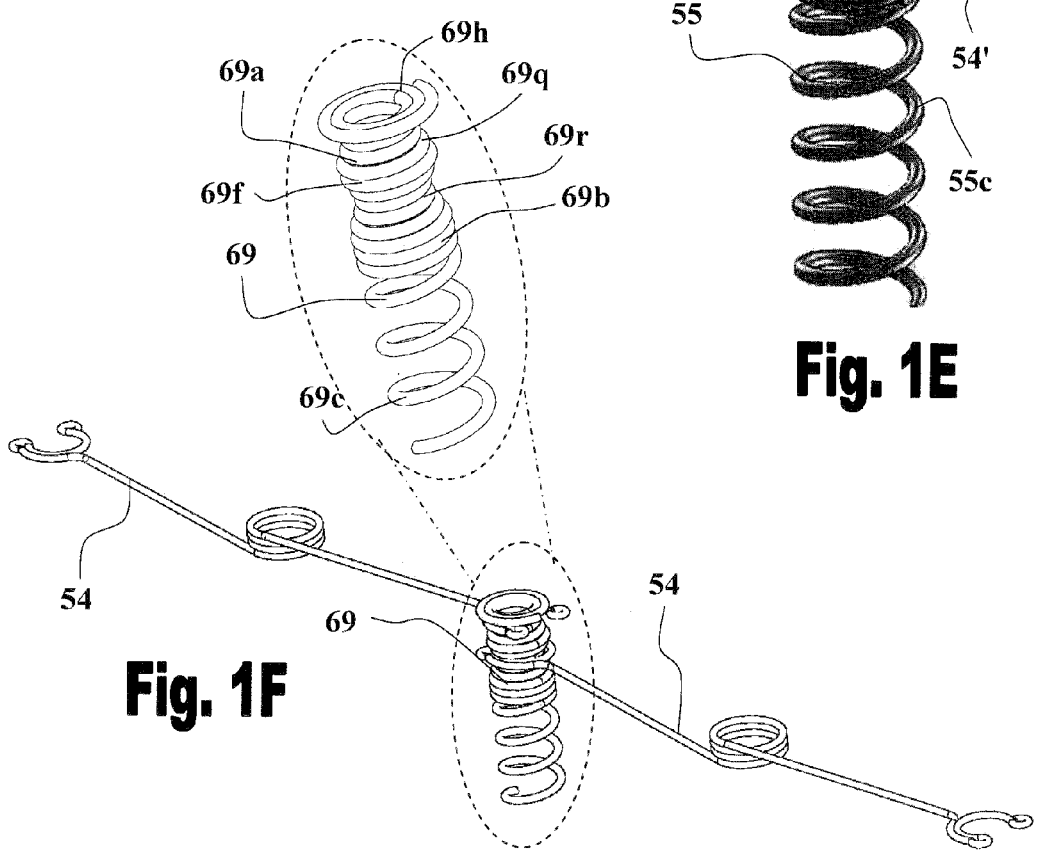
Figure 1G:
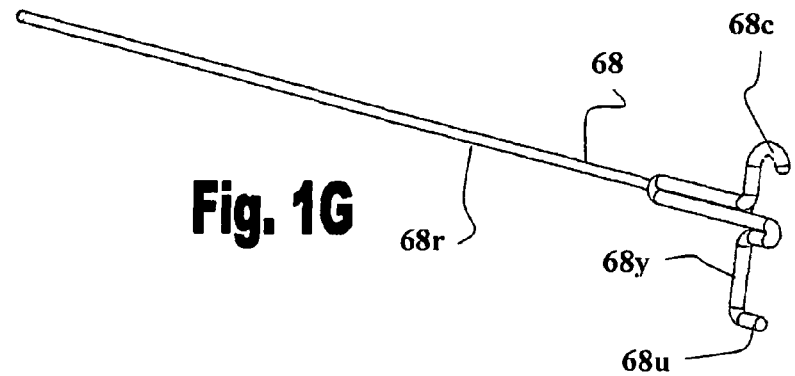
FIG. 1G shows a perspective view of a tool for guiding in the positioning of the attachment means.
Figure 1H:
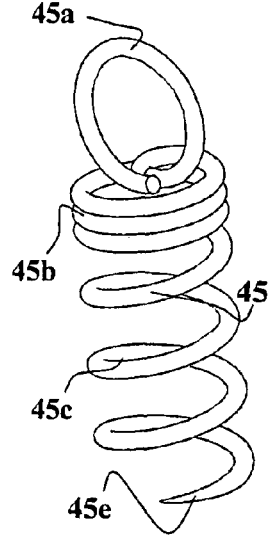
FIG. 1H shows a perspective view of the attachment means used in FIG. 1B, FIGS. 1I to 1N show various views and exemplify the use of a tool for attaching the attachment means of the invention to the wall of the heart.

As best seen in FIG. 1H, anchoring means 45 comprise a head section 45a, a neck section 45b and an attachment section 45c. Anchoring means 45 are preferably made from a curved wire, wherein the attachment section 45c is curved in a helix (spring) shape ending in a sharp tip for facilitating threading thereof into the wall of the heart. Near the neck section 45b of the anchoring means 45 the distances between the helix loops are reduced abruptly to form the neck section 45b, which acts as a stopper to prevent excess threading of anchoring means 45.

Anchoring means 45 may be used for delivering medicaments into the tissue into which it is threaded. In such implementation the attachment section 45b of anchoring means 45 may be coated by one or more layers of therapeutic medicaments, or alternatively, the attachment section 45b may be prepared to include an internal lumen, suitable for maintaining said medicaments thereinside, and release aperture communicating with said internal lumen, for releasing the medicaments into the tissue therethrough. These drug delivery implementations may be designed for providing delayed drug delivery to the tissue.

As exemplified in FIG. 1B, anchoring means 45 may be employed for delivering electrical signal to the heart tissue by connecting a pacemaker 85 thereto. Pacemaker 85 is a type of conventional pacemaker device which uses electrical impulses, typically delivered by electrodes contacting the heart muscles, to regulate heart beats. The primary purpose of pacemaker 85 is to maintain an adequate heart rate, either since the heart's natural pacemaker (the sinus node) is not functioning properly (i.e., slow heart beats), or if there is a block in the heart's electrical conduction system. In some cases it may be advantageous to combine with pacemaker 85 an implantable defibrillators, which is integrated into a single implantable device. Other possible implementations may include multiple electrodes for stimulating different locations over the heart muscle to improve synchronization of the lower chambers of the heart. As shown in FIG. 1B, the pacemaker 85 is electrically connected to loop 45a of anchoring means 45 by means of electrical cable 85w, wherein anchoring means 45 is implanted in the heart tissue and used as an electrical conductor for delivering the electric signals produced by pacemaker 85 to the heart tissue.

It should be understood that pacemaker 85 may be implanted together with ventricular function assisting device employing anchoring means 45, or alternatively, it may be implanted later, if required. Pacemaker 85 is implanted in the patient's body in substantially the same way as in conventional pacemaker procedures, such that it may be placed under the chest or abdomen skin of the patient, but instead of using the conventional pacemaker electrodes the electrical signals it produces are delivered to the patient's heart through anchoring means 45.

The head section 45a is formed in a shape of a loop through which the "G"-shaped anchoring loops 43a of the elastic elements 43 can be passed to engage the same therein. Head section 45a may be formed in any suitable geometrical shape e.g., circular, elliptic, rectangular, however, in this preferred embodiment the head section 45a is formed in a shape of a ring.

Anchoring means 45 (also shown in FIG. 1H) can be threaded into the wall of the heart by rotation. The attachment method of elastic elements 43 and anchoring means 45 is shown in FIG. 1B, wherein two elastic elements 43 are mounted by means of attachment elements 45.

Elastic element 43 may be manufactured using conventional wire (e.g., having circular, elliptic, or rectangular/polygonal cross section) curving techniques, photo chemical etching techniques, laser cutting, or by an erosion process (e.g., using tin films) from a type of elastic metal or plastic, such as, but not limited to, Nitinol, stainless steel, silicon, or a suitable alloy, composite compound, or absolvable material (e.g., PLLA, PGA, or PLA), preferably from a Cobalt alloy, having a diameter (thickness) of about 0.45 mm. The length of the arms of elastic element 43 may generally be in the range of 20 to 30 mm, preferably about 23 mm, and the angle $\alpha$ therebetween is about 165±5°. The diameter of torsion loop(s) may generally be in the range of 3.5 mm (for elastic elements mounted at the extremities of the lined sequence) to 5.7 mm, and the diameter of the "G"-shaped anchoring loops 43a is preferably about 2±1 mm.

Anchoring means 45 may be manufactured by using conventional spring manufacturing techniques, wire curving processes which may be followed by a suitable thermal treatment to set mechanical characteristics and relax curving tensions. Anchoring means 45 may be manufactured from a type of metal or plastic material, such as, but not limited to, Nitinol, stainless steel, silicon, or a suitable alloy, composite compound, or absolvable material (e.g., PLLA, PGA, or PLA), preferably from, a Cobalt alloy. Most preferably, anchoring means 45 are made from a turned wire having thickness of about 0.45 mm and made of a Cobalt alloy. The total length of anchoring means 45 may generally be in the range of 8 to 18 mm, preferably about 15 mm. The diameter of the helix loops in the attachment section 45c may generally be in the range of 3 to 6 mm, preferably about 5 mm, the distance between consecutive loops thereof may generally be in the range of 1 to 3 mm, preferably about 2 mm, and the length of said attachment section may generally be in the range of 6 to 12 mm, preferably about 8 mm. The diameter of the neck section 45b may generally be in the range of 2 to 6 mm, preferably about 5 mm, and its length may generally be in the range of 0.5 to 2 mm, preferably about 1.5 mm.

A product comprising elastic elements and anchoring means suitable for ventricular function assisting device 40 is sold under the ImCardia trademark of CorAssist cardiovascular Ltd., Israel.

Another possible configuration of elastic elements and anchoring means is depicted in FIGS. 1C to 1F. In this preferred embodiment the attachment section 53c and the neck section 53b of the anchoring means 53 are made from a curved wire, while its head section 53m is made from a flanged rod comprising a flanged base 53g adapted to firmly fit into the loops of neck section 53b, a flanged top 53h, and a middle flange 53f therebetween. The gaps 53q and 53r respectively obtained in head section 53m between flanged base 53g and middle flange 53f, and between flanged top 53h and middle flange 53f, are adapted to receive "C"-shaped graspers 54u of elastic element 54. Elastic element 54 is preferably a type of torsion spring made from an elastic wire formed in a "V"-like shape, having torsion loop(s) 54r at its apex and "C"-shaped graspers 54u at the end of its arms 54a. The wire at the tips of "C"-shaped graspers 43a is preferably shaped to form fastening loops 54q adapted to provide firm attachment over the flanged rod 53m. Flanged rod 53m is preferably attached to neck section 53b of anchoring means 53 by welding.

FIG. 1F demonstrates attachment of neighboring elastic elements 54 to a mutual anchoring means 69. The attachment section 69c, neck section 69b and head section 69a, of anchoring means 69 are preferably made from a single wire turned such that the shape of head section 69a is similar to the shape of flanged rod (53m) in anchoring means 53, by forming an expanded top 69h and expanded middle 69f such that corresponding gaps 69q and 69r are obtained suitable for receiving the graspers of the elastic element.

FIG. 1E illustrates one preferred embodiment of an anchoring means 55 having attachment section 55c and neck section 55b made from a curved wire, and a head section 55m made from a flanged rod, as in anchoring means 53 (shown in FIG. 1D) described hereinabove, and further comprising domelike top 55z screwed into the flanged top 55h of anchoring means 55 for protecting and preventing tissue injury. In this example elastic elements 54' are attached to anchoring means 55 by means of closed loops provided on its arms and which are fitted into the gaps formed in head section 55m. Elastic elements 54' and anchoring means 53 may be manufactured from similar materials, and by means of similar techniques, as in the respective means previously described hereinabove.

FIG. 1G shows a perspective view of a guiding tool 68 suitable for guiding the operator in the positioning of the anchoring means of the invention. Guiding tool 68 comprises an elongated handle 68r and a locator portion 68y attached to its distal end. Locator portion 68y comprises two perpendicular arms used for designating the distance between adjacent anchoring means. In use, the arm having a curved end 68c will typically be engaged in the attachment section of the anchoring means (e.g., 45c of anchoring means 45) while the arm comprising the vertical ending 68u will be used to guide the operator in determining a location for a new anchoring means to be attached. Guiding tool 68 may be manufactured from stainless steel, nitinol, or from a biocompatible alloy, by extrusion or a metal working process, for example. The length of guiding tool 68 may generally be in the range of 180-200 mm, its diameter about 1 to 2 mm, and the width of locator portion 68y may be about 30 to 70 mm.

Figure 1I:
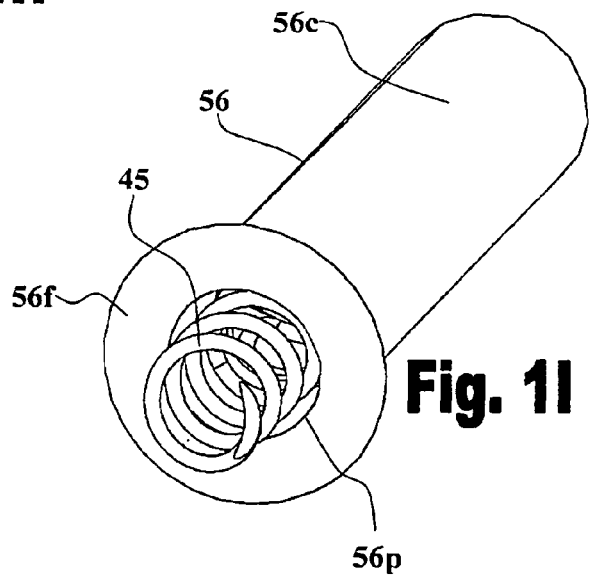
Figure 1J:
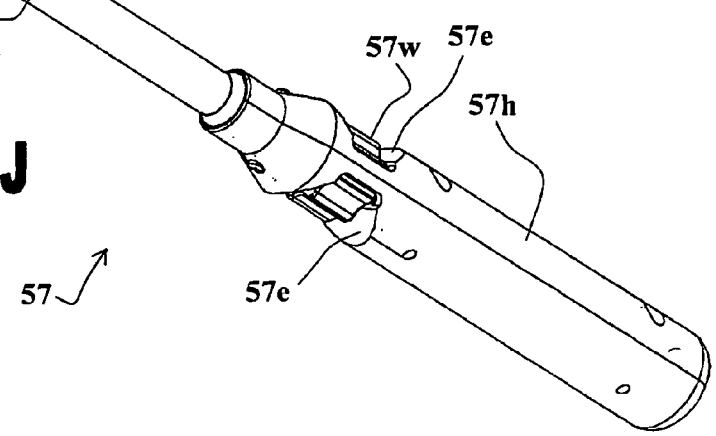

FIGS. 1H to 1O illustrate and demonstrate attachment of the anchoring means 45 depicted in FIG. 1H by means of a screwing tool 57. With reference to FIG. 1J, screwing tool 57 comprises a proximal handle 57h to which there is attached a hollow shaft 57s having a hinged head 57d connected thereto by hinge 57i. Proximal handle 57h comprises a rotatable wheel 57w mounted in depressions 57e provided in opposing sides of proximal handle 57h. Screwing tool 57 may further comprise a foldable locator 57g for aiding the operator in determining locations for screwing the anchoring means 45 over the heart wall. In FIG. 1J foldable locator 57g is shown in its deployed state, if however it is not needed, it may be rotated about the hinges connecting it to hinged head 57d, such that it is placed over and aligned with a side surface thereof.

With reference to FIG. 1L, illustrating a sectional view of screwing tool 57, hinged head 57d comprises a distal opening 57o adapted to receive and hold a holding cup 56 in which anchoring means 45 is held by means of a fastening rod 58. The base of holding cup 56 is firmly received in rotatable holder 57z rotatably mounted inside hinged head 57d, on its base. Hollow shaft 57s comprises a rotatable rod 57q placed thereinside mechanically linked to rotatable wheel 57w. At the distal end of rotatable rod 57q there is attached one end of a wire (or flexible rod) 57r, which other end is attached to rotatable holder 57z provided inside hinged head 57d. In this way rotary motion of wheel 57w is delivered via rod 57q and wire 57w to rotatable holder 57z, which in turn delivers the rotary motion to the fastening rod 58 and anchoring means 45 assembly held by holding cup 56.

FIG. 1K shows a perspective view of fastening rod 58 having an anchoring means 45 attached to it. As shown, fastening rod 58 comprises a central slit 58s passing along a longitudinal section of its length. Central slit 58s is adapted to receive and firmly hold the head section (45a) of anchoring means 45. FIG. 1I shows a perspective view of holding cup 56 holding a fastening rod 58 (not shown) and anchoring means 45 assembly, wherein it is seen that holding cup 56 is made from a generally a cylindrical element 56c having flanged edge 56f over its opening 56p, which is adapted to receive said fastening rod 58 and anchoring means 45 assembly.

FIGS. 1M and 1N, are exemplifying attachment of anchoring means by means of screwing tool 57. During this process the operator adjusts the angle of hinged head 57d to allow its front side to face and access the heart 10, and then the anchoring window 57n of locator 57g is placed over a previously placed anchoring means 45, thus providing a tolerance for determining a suitable location for attaching the new anchoring means. Once the new location is determined the operator gently presses the front side of hinged head 57d of screwing tool 57 against the wall of the heart 10 and rotates wheel 57w, thereby screwing anchoring means 45 into the tissue.

Screwing tool 57 may be manufactured from stainless steel, Teflon, nitinol, polycarbonate, silicon, medical grade delrin, medical grade nylon, or from a biocompatible alloy, by means of extrusion, rapid prototyping, or metal working, for example. The length of screwing tool 57 may generally be about 200-500 mm and its diameter about 10-40 mm.

FIGS. 1O to 1Q illustrate a preferred embodiment of a tool 60 designed for delivering and attaching several anchoring means 45 stacked in series inside its hollow shaft 60s configured as a stack having a longitudinal slit 60i along its length adapted to slidably hold the head sections (45a) of anchoring means 45. The anchoring means 45 are pushed distally by spring 60p and the most distal anchoring means 45 stacked inside shaft 60s is attached to a screwing head 60t configured to hold the head section 45a of the anchoring means 45 and rotate it when push-button 60d in proximal handle 60h is pressed by the operator. Whenever pressed down, push-button 60d activates an electrical motor (not shown) configured to deliver rotational motion to screwing head 60t.

As seen in FIG. 1O, tool 60 further comprises a movable rod 60a passing along the length of its bottom side, said movable rod 60a is mechanically linked to slider 60r. With reference to FIG. 1Q, showing a top view of the proximal section of tool 60, slider 60a may be changed between two operation states, by retaining it in lateral slit 60q or in lateral slit 60r. Locator 60W is placed over a previously placed anchoring means 45, thus providing an anchor for determining a suitable location for attaching the new anchoring means. Once the new location is determined the operator gently push the movable rod 60a into the lateral slit 60q and push-button 60d in proximal handle 60h to operate the delivery tool 60 for implantation a new anchoring means 45.

As seen in FIG. 1O, the distal part of hollow shaft 60s may comprise optical guiding means 60g mounted on opposing sides thereof and adapted to emit light beams (e.g., by means of low-energy laser diodes) set in proper angles such that one light beam can point to a new location for placing a new anchoring means whenever the other light beam is placed over the location of a previously placed anchoring means, thereby aiding the operator in determining a proper distance between the anchoring means.

It is noted that the delivery tools 57 and 61 described hereinabove may be easily modified for delivering and attaching various embodiments of the anchoring means, such as anchoring means 69 (shown in FIG. 1F), anchoring means 53 (shown in FIG. 1D), described hereinabove, and modifications thereof.

FIGS. 1R to 1T show various views of a delivery tool 59 designed for delivering an elastic element 43 (or other such elastic elements, such as for example, 43 shown in FIG. 1A, 54 shown in FIG. 1C, or 54' shown in FIG. 1E) and attaching the same over previously placed anchoring means in a minimally invasive procedure. With reference to FIG. 1R, delivery tool 59 comprises a hollow handle 59h having a longitudinal slit 59s passing along a portion of its length in which there is movably placed a slider element 59p, a slidable shaft 59f extending distally therefrom and which proximal portion is placed inside hollow handle 59h and mechanically linked to slider element 59p by means of slidable connector 59c, and a longitudinal rod 59r fixedly attached to handle 59h at 59n and passing inside, and along the entire lengths of, hollow handle 59h and slidable shaft 59f. The distal end of longitudinal rod 59r comprises a retaining part 59k configured to receive and hold the torsion loop(s) (30) of the elastic element.

As seen in FIG. 1R longitudinal slit 59s comprises a proximal recess 59b and a distal recess 59y in each of which slider element may be placed. In a first state of device 59, shown in FIGS. 1R to 1T, slider element 59p is held in proximal recess 59b, in which state slidable shaft 59f is pulled proximally such that retaining part 59k is exposed through distal end opening of slidable shaft 59f. In a second state of device 59 (not shown) slider element 59p is held in distal recess 59y, in which state slidable shaft 59f is pushed distally such that slidable shaft 59f is pushed distally and retaining part 59k is introduced into chamber 59g provided inside slidable shaft 59f at its distal end.

In FIG. 1T there is shown an enlarged view of the distal portion of delivery tool 59 when an elastic element 43 is retained in its retaining part 59k. As seen, retaining part 59k comprises of flat section 59e on which there is a holding shoulder 59y which upper protrusion is facing slidable sheath 59f, and a tooth 59x formed at its distal end. The distance between shoulder 59y and tooth 59x is configured such that torsion loop(s) 30 of the elastic element 43 are retained thereover by placing apex of the "V"-shaped elastic element 43 under the upper protrusion of shoulder 59y and the opposing side of torsion loop(s) 30 over tooth 59x. In this way, when slider element is placed in distal recess 59y slidable shaft 59f is pushed over retaining part 59k and elastic element 43 held by it, such that arms 14a and 14b of elastic element 43 are bent distally into chamber 59g.

In this way the elastic element 43 is delivered in a folded state (not shown) through a small incision and attached to the anchoring means previously placed on the heart by placing the distal end of tool 59 near the previously attached anchoring means and moving slider element 59p back to proximal recess 59b, which in turn retracts slidable shaft 59f proximally and exposes elastic element out of chamber 59g. The operator then simply maneuvers tool 59 and slider element 59p for properly engaging "G"-shaped anchoring loops 43a of elastic element 43 (or C-shaped graspers 54u of elastic element 54) in head sections 45a of anchoring means 45, as illustrated in FIG. 1B.

Delivery tool 59 may be manufactured from stainless steel, Teflon, nitinol, polycarbonate, silicon, medical grade delrin, medical grade nylon, or from a biocompatible alloy, by means of extrusion, rapid prototyping, or metal working, for example. The length of delivery tool 59 may generally be about 200-500 mm and its diameter about 10-40 mm.

FIG. 1U shows a perspective view of one preferred embodiment of ventricular function assisting device 40. Device 40 is configured to encircle the heart 10 (shown in FIG. 1V) by at least two, upper and lower, restrictive elements, 41a and 41b, respectively. The upper and lower restrictive elements, 41a and 41b, are connected by means of springs 46 to a set of vertical bars 47 equally distributed about the perimeters of restrictive elements 41a and 41b. Springs 46 may be pulling and/or pushing springs and they are mainly used when device 40 is operated in the second mode of operation i.e., after restrictive elements, 41a and 41b, are secured to the wall of the heart by means of fastening mechanisms, 42a and 42b, respectively. Vertical bars 47 are preferably curved according to the curvature of the heart, but the may also be flexible enough to allow them to easily curve and assume a curvature more or less similar to the curvature of the heart.

Vertical bars 47 are attached to the wall of the heart by means of anchoring means 45 threaded into the wall of the heart 10 along their lengths. Vertical bars 47 are passed through the head sections (45a) of anchoring means 45, such that minimal or negligibly small forces are applied over the wall of the heart by vertical bars 47 at the attachment points of anchoring means 45 when device 40 is operated in the first mode of operation.

The portion of device 40 mounted over the left ventricle further comprises elastic elements 43 which are mounted more or less horizontally between pairs of adjacent anchoring means 45 attached to the wall of ventricle. Restrictive elements, 41a and 41b, comprises a fastening mechanisms, 42a and 42b, respectively, which are initially in a state which allows encircling the heart by restrictive elements 41a and 41b without engaging the heart by said restrictive elements 41a and 41b. Fastening mechanisms 42a and 42b are configured to allow fastening restrictive elements over heart 10 at a later time after the mounting procedure of device 40 on the heart is completed.

In this way the operation of device 40 may be changed into its second mode of operation whenever needed, particularly if the patient develops systolic dysfunctions. The activation of fastening mechanisms, 42a and 42b, may be carried out by a minimally invasive procedure, for example, via a small incision, by connecting access tubes to device 40 each having one opening near fastening mechanism (e.g., 42a) and another opening being externally accessible by the practitioner such that suitable instruments (e.g., clamps, tweezers) may be introduced therethrough for fastening restrictive elements over the heart.

FIG. 1V show the ventricular function assisting device 40 illustrated in FIG. 1U, when mounted on a heart 10. FIG. 1W illustrates a possible implementation of a locking mechanism 42a (or 42b) suitable for fastening the ventricular function assisting device 40 over the heart 10. In this implementation a pulling spring 50 is mounted over a gap 41g in restrictive element 41a. Pulling spring 50 may be mounted by means of two socket members 51 formed, or attached, on restrictive element 41a near gap 41g, and having respective sockets 51s capable of receiving spring ends 50e and securing the same to restrictive element 41a.

Locking mechanism 42a further comprises a supporting bar 52 configured to attach to restrictive element 41a over the opening of gap 41g. In this way gap 41g is maintained in restrictive element 41a due to supporting bar 52, which prevents its closure by pulling spring 50. Supporting bar 52 comprises attachment pins 52b provided at its ends, said attachment pins 52b are more or less perpendicular to supporting bar 52 for allowing them to be received in respective sockets 41s provided in the opposing sides of restrictive element 41a, having gap 41g there between. Grip 52g is attached, or formed, perpendicular to supporting bar 52 more or less about its center, for providing the practitioner a convenient grip for removing supporting bar 52 when the fastening of restrictive element 41a over heart 10 by the closure of gap 41g is needed, as shown in FIG. 1X. Conveniently, grip 52g may include a head portion 52h for improving the grip there over.

Restrictive elements 41 may be manufactured from a biocompatible metallic alloy, for example, from stainless steel or from a biocompatible polymer, for example silicon, preferably from stainless steel. The lengths of restrictive elements 41 should be adjusted according to the size of the treated heart, for example, the length of upper restrictive element 41a may generally be in the range of 115 to 145 mm, preferably about 125 mm, and the length of lower restrictive elements 41b may generally be in the range of 10 to 120 mm, preferably about 50 mm.

Vertical bars 47 may be manufactured from a biocompatible metallic alloy, for example stainless steel or Conichrome (fwm 1058) or from a biocompatible polymer, for example silicon, preferably from stainless steel. The lengths of vertical bars 47 may generally be in the range of 70 to 120 mm, preferably about 90 mm. Springs 46 are preferably small springs made from a biocompatible metal alloy, for example stainless steel or Conichrome (fwm 1058), configured to apply forces in the range of 0.7 to 1.2 N.

Referring now to FIG. 1W, Pulling spring 50 is preferably made from an elastic wire having a diameter generally in the range of 0.3 to 0.7 mm, preferably about 0.5 mm, and it is preferably made flat (e.g., having elliptic or rectangular spring loops) in its cross-sectional profile. Spring 50 may be manufactured by conventional spring manufacture techniques, from a type of biocompatible metallic alloy, for example stainless steel or Conichrome (fwm 1058), preferably from Conichrome. The length of spring 50 may generally be in the range of 10 to 20 mm, preferably about 15 mm.

Gap 41g may generally be in the range of 5 to 20 mm, preferably about 10 mm. Supporting bar 52 may be manufactured from a biocompatible metallic alloy, for example stainless steel or Conichrome (fwm 1058), preferably from Conichrome. The diameter of supporting bar 52 may generally be in the range of 1 to 3 mm, preferably about 2 mm, and its length should be fitted to the length of gap 41g.

Ventricular function assisting device 40 may be mounted on the heart of a treated subject in a procedure comprising the following steps: first in open chest surgery followed by thoracotomy, and at a later stage, when the systolic device needs to be functional, this may be performed utilizing minimal invasive thoracoscopy procedure. Normally, device 40 will be installed in its first mode of operation for treating diastolic dysfunctions. If at a later time the patient develops systolic dysfunction ailments the state of the device may be changed to operate in its second mode of operation by fastening restrictive elements 41 over the heart. The fastening of restrictive elements 41 may be carried out as follows: pull out the pin 52 by minimal invasive procedure and thereby causing restrictive elements 41 to fasten over the heart automatically.

Of course, device 40 may be installed on the heart of a treated subject initially in its second mode of operation, if treatment of both, diastolic and systolic dysfunctions is required.

In the example illustrated in FIGS. 1C and 1D, only two restrictive elements (41a and 41b) are shown, however, it should be clear that embodiments of the invention may include more than two such elements.

FIGS. 2A and 2B schematically illustrate an embodiment of the ventricular function assisting device 61 for treating systolic and diastolic dysfunctions, in which the restrictive elements 65a and 65b are implemented by tension springs (for example, having a wavy configuration) which increase their elasticity. Although in the figures only two such restrictive elements are illustrated, it should be clear that embodiments of the invention may include more than two such elements. FIG. 2A shows the side of device 61 which is installed over the right ventricle and FIG. 2B shows the other side of the device, which is installed over the left ventricle of the heart. In this embodiment vertical bars 47 may be connected directly to tension springs 65a and 65b, or by means of springs (not shown), as exemplified in FIGS. 1C and 1D.

Device 61 may be installed on the wall of the heart of a treated subject by means of anchoring means 45, as exemplified in FIGS. 1A to 1D, and can partially or completely circumvent the heart. Preferably, the operation of device 61 may be changed between two operation modes by means of fastening mechanisms (e.g., 42a demonstrated in FIGS. 1W and 1X) provided in its restrictive elements 65a and 65b (not shown), as exemplified hereinabove.

Alternatively, the embodiment shown in FIGS. 2A and 2B the ventricular function assisting devices 61 may be operated in only one mode of operation, in which both diastolic and systolic dysfunctions are treated. Namely, after device 61 is installed on the wall of the heart of the patient, the operations of both the elastic elements 43 and of the restrictive elements 65a are effective.

FIGS. 3A and 3B schematically illustrate ventricular function assisting devices, 63 and 64, respectively, for treating systolic and diastolic dysfunctions, which employ intermediate restrictive elements, 65c and 41c, respectively. In these embodiments shorter vertical bars 47s are used for connecting between the restrictive elements. For example, in FIG. 3A, vertical bars 47s are used for connecting upper restrictive element 65a to intermediate restrictive element 65c, and for connecting lower restrictive element 65b to intermediate restrictive element 65c. As previously explained, any number of such restrictive elements may be used, and the number of elements shown in FIGS. 3A and 3B is provided by way of example only.

Vertical bars 47s may be connected to the restrictive elements by means of springs 46s. Furthermore, the lengths of vertical bars 47s connecting between the upper restrictive element (e.g., 41a) and the intermediate restrictive element (41c) may be different from the lengths of vertical bars 47s connecting between the lower restrictive element (e.g., 41b) and the intermediate restrictive element (41c).

In the device 63 shown in FIG. 3A restrictive elements 65 have a wavy configuration for increasing their elasticity. Restrictive elements 65a, 65b and 65c, may be manufactured from a cobalt alloy or stainless steel, preferably from Conichrome (fwm 1058). As in the embodiment illustrated in FIGS. 2A and 2B, device 63 may be operated in only the second mode of operation, in which both diastolic and systolic dysfunctions are treated. Device 63 may be similarly attached to the wall of the heart by means of anchoring means (45 not shown).

The device 64 shown in FIG. 3B is principally similar to the device shown in FIGS. 2A to 2D, where the main differences are in the use of intermediate restrictive element 41c, and connecting the same to restrictive elements 41a and 41b by means of shorter vertical bars 47s.

FIGS. 4A to 4C schematically illustrates an implementation of a ventricular function assisting device 77 for treating combined systolic and diastolic dysfunctions which is configured to enclose the apex of the heart 10. As illustrated in the perspective view shown in FIG. 4A, device 77 comprises a single restrictive element 41, and as more clearly seen in the side view shown in FIG. 4C, vertical bars 47 are forming a closed connection point 48 at the bottom of device 77 (e.g., by means of cylinder pivot or a kind of joint).

FIG. 4B schematically illustrates a possible fastening mechanism based on threading. In this example, the fastening mechanism is based on a simple screw tightening method (e.g., gear clamp), wherein screw 42t is used for tightening (or for loosening) restrictive element 41 about heart 10. This mechanism may be manufactured from biocompatible materials similar to those discussed hereinabove, preferably from stainless steel, employing conventional standard manufacture techniques.

Figures 5A, 5B:
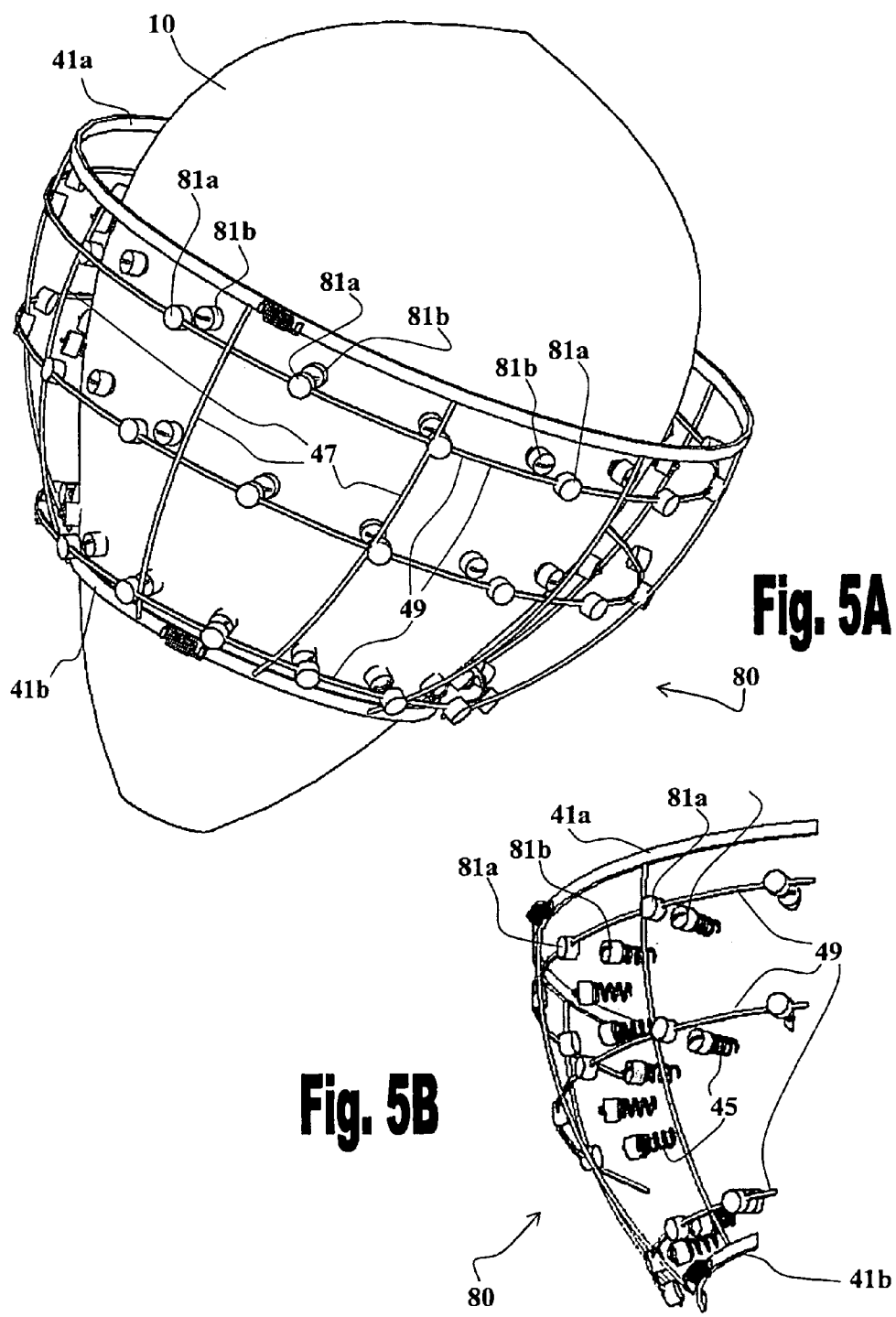
FIGS. 5A and 5B schematically illustrate a device for treating systolic and diastolic dysfunctions which is based on a magnetic/electromagnetic mechanism.

FIGS. 5A and 5B schematically illustrate a device 80 for treating systolic and diastolic dysfunctions which is based on a magnetic mechanism. Device 80 comprises an upper restrictive element 41a and a lower restrictive element 41b which are connected by means of curved vertical bars 47. Vertical bars 47 provide a support for a set of one or more horizontal rings 49 encircling heart 10. Each horizontal ring 49 comprises a set of electromagnets 81a, each of which is connected to a controllable power source (e.g., current source, piezoelectric, not shown). A corresponding set of permanent magnets 81b is attached to the wall of the heart 10 opposite to electromagnets 81a, such that pairs of adjacent electromagnets 81a and permanent magnets 81b are obtained.

As exemplified in FIG. 5B, which shows a portion of device 80 without heart 10, permanent magnets 81b may be attached to the wall of the heart 10 by means of anchoring means 45, or by a modification or any of the various variations thereof exemplified hereinabove, adjusted to include a permanent magnet 81b at their head section (45a not shown). Control means (not shown) is used to control the operation of the power source used for energizing electromagnets 81. In cases of systolic dysfunctions, during systole, the control means operates the power source to activate electromagnets 81a such that the polarity of the magnetic field produced thereby causes repulsion forces to evolve between electromagnets 81a and permanent magnets 81b, in order to assist the systolic heart contraction. In cases of diastolic dysfunctions, during diastole, the control means operates the power source to activate electromagnets 81a such that the polarity of the magnetic field produced thereby causes attraction forces to evolve between electromagnets 81a and permanent magnets 81b, and thereby assist in the diastolic heart expansion.

Of course, the operation of the electromagnets should be synchronized with the heart activity. The synchronization may be achieved by monitoring ECG signal, signals received from a pacemaker, or by means of a suitable internal sensor.

Horizontal rings 49 may be manufactured from the same material of vertical bars 47, and they may be attached to said vertical bars 47 by a rigid or non-rigid connection. The pairs of electromagnets 81a and permanent magnets 81b are adapted to produce repulsion/attraction forces generally in the range of 0.7 to 1.2 N. Permanent magnets 81b may be manufactured from a magnet with biocompatible cover. Electromagnets 81a may be implemented by small coils having a core made from a paramagnetic or ferromagnetic material (e.g., magnesium, molybdenum, lithium, or tantalum); said coils may be manufactured from copper. The distances between electromagnets 81a and permanent magnets 81b may generally be in the range of 0 to 10 mm.

In another preferred embodiment of the invention the ventricular function assisting device is based on a plunger mechanism designed to—i) augment the relaxation of the left ventricle of the heart during diastolic phase, which assists in reducing the pressure thereinside and in pumping blood thereinto; and ii) help the left ventricle during systolic function, to pump out the blood from said ventricle.

The plunger mechanism device generally consists of two hollow sections, a front section and a rear section, which interiors are communicated by a mutual opening, wherein said hollow sections comprise mechanically linked slidable plungers installed in each of said sections. The hollow sections and their respective plungers are aligned along a longitudinal axis of the device (also referred to as axis of movement) such that said plungers are free to move thereinside along said longitudinal axis. The plungers are mechanically linked to an elastic or shape memory device, preferably in a form of a spring, which is adapted for applying mechanical forces on said plungers for sliding the same in their respective sections.

The front and rear hollow sections of the device are designed to communicate with a chamber of the heart and to pump in, and pump out, volumes of blood from/to said chamber. The front hollow section of the device comprises a front opening, preferably aligned with the axis of movement of the plungers, adapted to communicate with a chamber of the heart via a first aperture in the wall of the heart. The rear hollow section of the device comprises a lateral opening which is adapted to communicate with the chamber of the heart via a tube, said tube being connected to said lateral opening at one end thereof and to a second aperture in the wall of the heart by another end thereof.

The plungers may be mechanically linked by a rod connecting between the centers of said plungers. The surface areas of the plungers are designed such that different forces are applied thereover responsive to the pressure in the chamber of the heart to which the device is connected. More particularly, the surface area of the plunger installed in the front hollow section is configured to be smaller than the surface area of the plunger installed in the rear hollow section of the device, and the cross sectional area of said hollow sections is configured correspondingly to snugly fit over said plungers. The elastic/shape memory device is adapted to apply mechanical forces over the plunger's assembly (the plungers and the rod connecting them) for pushing the same towards the rear section of the device.

The different surface areas of the plungers and the forces applied by the elastic/shape memory device are designed such that during diastolic function the forces applied over the front plunger by the blood pressure in the chamber of the heart and by the elastic/shape memory (pushing spring) device force the plungers assembly to move towards the rear section of the device, thereby increasing the volume of the heart chamber, assisting in pumping blood thereinto, and reducing the pressure thereinside. During the systole function, due to the increased blood pressure, the forces applied over the rear plunger are greater than the forces applied over the front plunger by the blood pressure and the elastic/shape memory (pushing spring) device, such that the plungers assembly is forced to move toward the front section of the device, thereby reducing the volume of the heart chamber and assisting in pumping out blood therefrom.

FIGS. 6A and 6B schematically illustrate the structure and operation of one preferred embodiment of a ventricular function assisting device 12 based on a plunger mechanism. Ventricular function assisting device 12 comprises a front hollow section 12f and a rear hollow section 12r having a mutual opening 12m connecting their interiors. Front plunger 14f is slidably installed inside front hollow section 12f, and rear plunger 14r is slidably installed inside rear hollow section 12r. Rod 15 is used for connecting the center of front plunger 14f to the center of the rear plunger 14r.

Front hollow section 12f of the device 12 comprises a front opening 12o adapted to communicate with the interior of the heart 10 via a first aperture 10b formed in heart 10. Support 19, preferably implemented by a rod, is mounted in front opening 12o to provide a support for spring 13 (pushing spring) mounted thereon, such that spring 13 is capable of applying mechanical forces over front plunger 14f along a longitudinal axis 6 of device 12. Tube 17 communicates with the interior of rear hollow section 12r via a lateral opening 12l provided in said rear section 12r. Tube 17 comprises an angled or curved section which more or less aligns opening 17o of tube 17 with opening 12o of front hollow section 12f. Opening 17o is adapted to communicate with the interior of heart 10 via a second aperture 10a formed in the wall of heart 10.

In one specific preferred embodiment of the invention (not shown) the pressure changes in heart 10 are affected inside ventricular function assisting device 12 via tube 17 by means of intermediate means, such that blood is not flown through the entire length of tube 17. In one possible implementation pressure sensors are used for measuring the pressure in the openings 12l and 10a, and pressure inside ventricular function assisting device 12 is adjusted accordingly. Alternatively, pressure changes may be affected in ventricular function assisting device 12 by filling tube 17 with a type of biological fluid (non compressible) capable of transferring the pressure changes into device 12. In yet another implementation, springs and plunger assembly may be used to transfer the pressure from lateral opening 12l to second aperture 10a.

The front and rear plungers, 14f and 14r, are designed such that different powers are applied there over by the blood pumped in and out of heart 10. For this purpose the surface area ($A_f$, e.g., 78 to 710 mm$^2$) of front plunger 14f is made smaller relative to the surface area ($A_r$, e.g., 78 to 710 mm$^2$) of rear plunger 14r. Spring 13 is configured to apply forces (e.g., $F_x$, e.g., 1 to 10 N) over front plunger 14f which enables the plungers assembly to slide along longitudinal axis 6 responsive to pressure variations in heart chamber to which the device is connected.

FIG. 6A illustrates the operation of the device 12 during the diastole, in which the pressure in the heart chamber is reduced such that the sum of forces applied over the front plunger 14f due to the diastolic pressure ($P_d$) in the heart chamber ($P_s \cdot A_f$) and by spring 13 ($F_x$), is greater than the force applied over rear plunger 12r due to said diastolic pressure ($P_d$) i.e., $P_d \cdot A_f + F_x > P_d \cdot A_r$. In response, the plungers' assembly (i.e., front plunger 14f, rear plunger 14r, and rod 15 connecting them) is forced to slide towards rear section 12r of device 12. As demonstrated by arrows 8i the rearward movement of the plungers assembly increases the chamber volume and assists in pumping blood thereinto. In response, portion of the blood in device 12 is discharged into heart 10, as demonstrated by arrows 7o.

FIG. 6B illustrates the operation of the device 12 during the systole, in which the pressure in the heart chamber is increased such that the sum of forces applied over the front plunger 14f due to the systolic pressure ($P_s$) in the chamber ($P_s \cdot S_f$) and by spring 13 ($F_x$), is smaller than the force applied over rear plunger 14r due to said systolic pressure ($P_s$) i.e., $P_s \cdot A_f + F_x < P_s \cdot A_r$. In response, the plunger assembly is forced to slide towards front section 12f of device 12. As demonstrated by arrows 8o, this movement of front plunger 14f assists in pumping out blood from the ventricle. In response, a volume of blood is pumped into device 12 via tube 17, as demonstrated by arrows 7i.

Figure 7A:
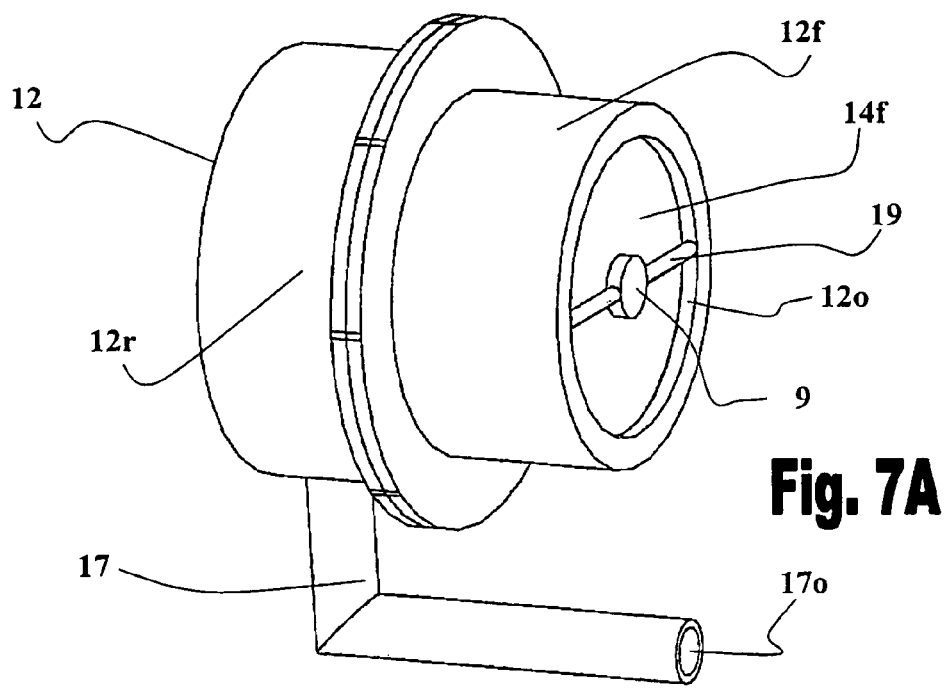
FIGS. 7A and 7B respectively show a perspective view and a sectional view of specific implementations of the ventricular function assisting device illustrated in FIGS. 6A and 6B.
Figure 7B:
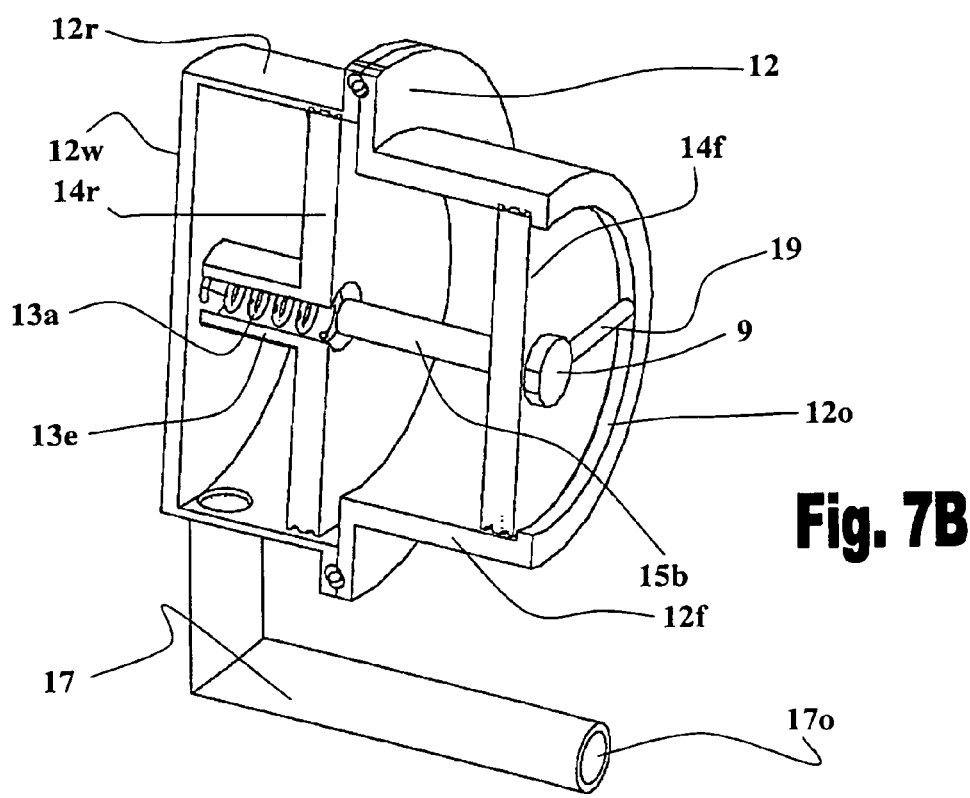

FIG. 7A shows a perspective view of a ventricular function assisting device 12, as illustrated in FIGS. 6A and 6B, wherein the front section 12f and the rear section 12r are implemented by two sealably connected hollow bodies. In this embodiment spring 13 (not shown) is mounted on a small disk 9 provided on supports 19. FIG. 7B is a longitudinal-section view illustrating an embodiment wherein pulling spring 13a is used, said pulling spring 13a is mounted in a spring enclosure 13e provided between rear plunger 14r and a rear wall 12w of rear section 12r. Spring 13a is sealably enclosed in spring enclosure 13e to prevent the blood moving in device 12 from contacting the spring.

Figure 8A:
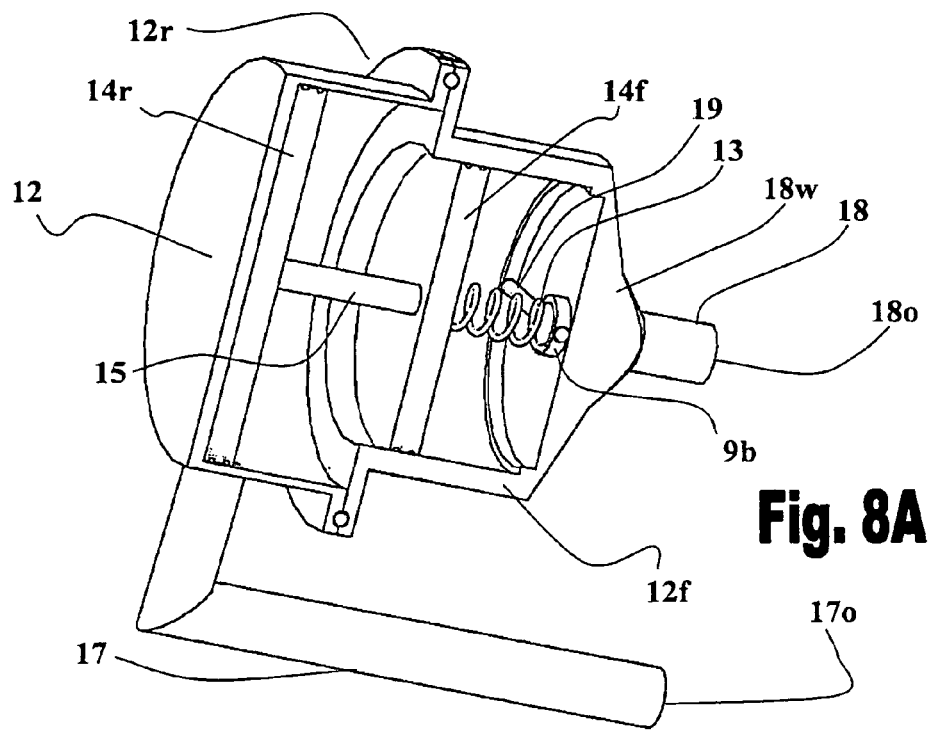

FIG. 8A is a longitudinal-section view of an embodiment of the diastolic function assisting device of the invention wherein the interior of the front section 12f communicates with the interior of the heart via a short tube 18. In this embodiment front section 12f comprises a front wall 18w used for closing the front side of front section 12f, wherein said front wall 18w has a tapering shape and comprises an opening (not shown) adapted to communicate with tube 18. Tube 18 and wall 18w are adapted to be attached to the wall of the heart 10, as illustrated in FIG. 8E. In this configuration Blood may be flown via an opening 18o of tube 18, into, or out from, device 12. FIG. 8E is a longitudinal section view of the embodiment shown in FIG. 8A showing said device mounted on the wall of the heart 10.

Figure 8B:
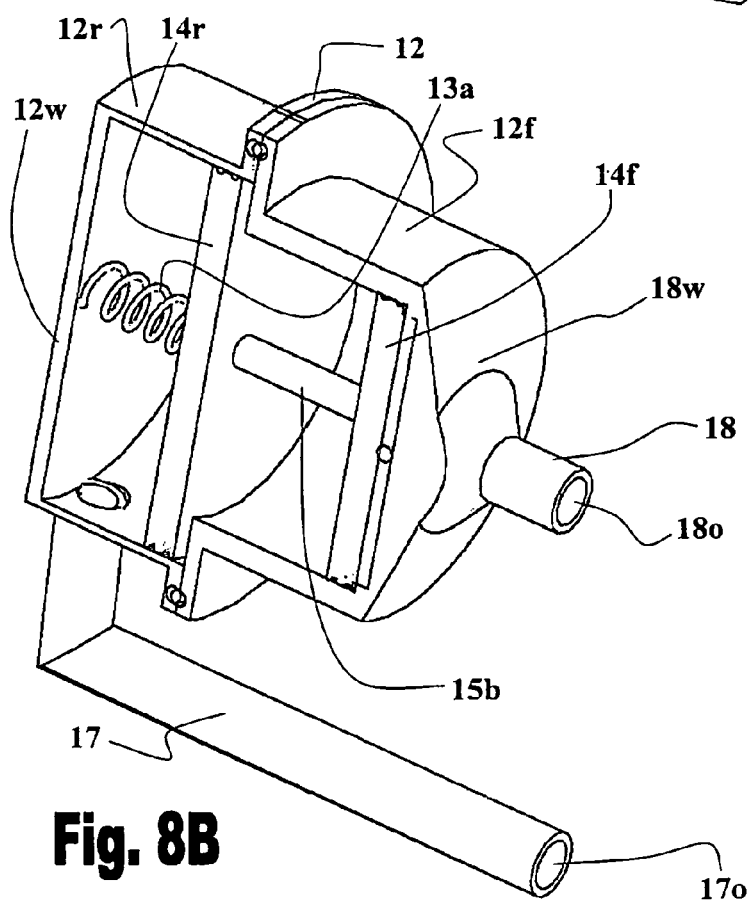
Figure 8E:
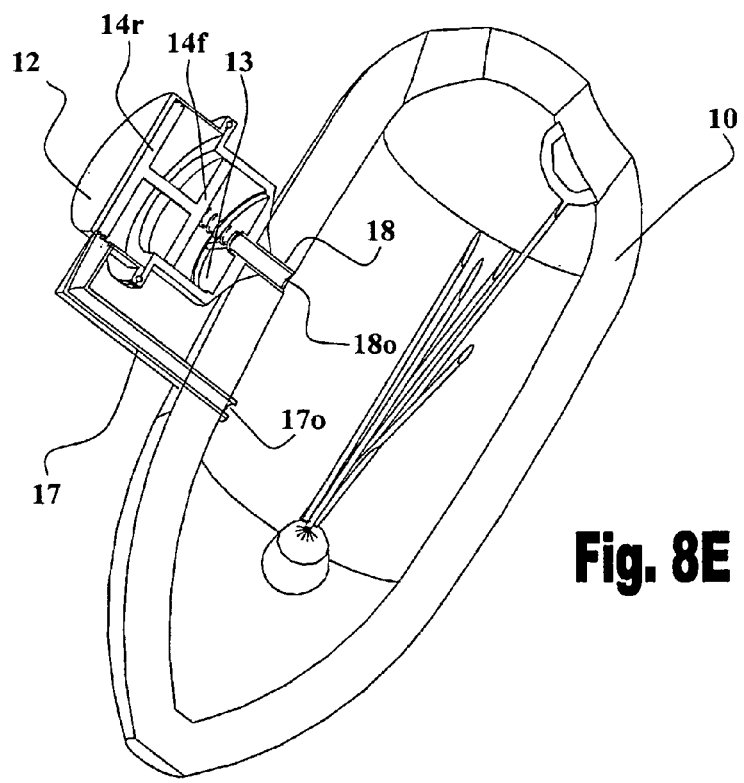

FIG. 8B is a longitudinal-section view illustrating an embodiment of device 12 configured to be connected to the wall of the heart 10 by means of front wall 18w and tube 18, as in FIG. 8A, wherein pulling spring 13a is used, said pulling spring 13a is mounted between rear plunger 14r and rear wall 12w of rear section 12r. FIG. 8C illustrates a longitudinal section view of this embodiment when mounted on a wall of heart 10.

FIG. 8D is a longitudinal-section view of an embodiment of device 12 configured to be connected to the wall of the heart 10 by means of front wall 18w and tube 18, as in FIG. 8A, wherein pulling spring 13a is mounted in a spring enclosure 13e between rear plunger 14r and rear wall 12w of rear section 12r. Spring enclosure 13e may be a type flexible tube made of silicon, polyurethane, or any kind of flexible polymer, suitable for sealing spring 13a and preventing blood from contacting it.

Ventricular function assisting device 12 may be manufactured, for example, by machining or injection, from type of biocompatible materials, such as for example, stainless steel, cobalt alloy, silicon, or Teflon, preferably from stainless steel. Spring 13 (or pulling spring 13a) may be manufactured from a suitable type of elastic or shape memory material, such as, but not limited to biocompatible metal alloy, preferably from stainless steel. The length of spring 13, or of pulling spring 13a, may generally be in the range of 5 to 25 mm, preferably about 15 mm, and its diameter may generally be about 0.1 to 1 mm.

Front hollow section 12f is preferably made from a cylindrical body having a diameter generally in the range of 10 to 30 mm and a length generally in the range of 5 to 25 mm. Rear hollow section 12r is preferably also made from a cylindrical body having a diameter generally in the range of 15 to 45 mm and a length generally in the range of 5 to 25 mm. Front and rear sections may be manufactured as integral parts of device 12, or alternatively, as separate parts which may be connected, for example, by means of screws.

Tube 17 is preferably manufactured as an integral part of rear section 12r, and it may be manufactured from the same material said rear section is made from. Similarly, tube 18 and front wall 18w are preferably manufactured as integral parts of front section 12f, and they are made from the same material from which said front section is made.

Front and rear plungers, 14f and 14r, may be implemented by bodies having a disk shape made from stainless steel or silicon, preferably from silicon, adapted to be slidably installed in front and rear hollow sections, 12f and 12r, respectively.

Figure 9A:
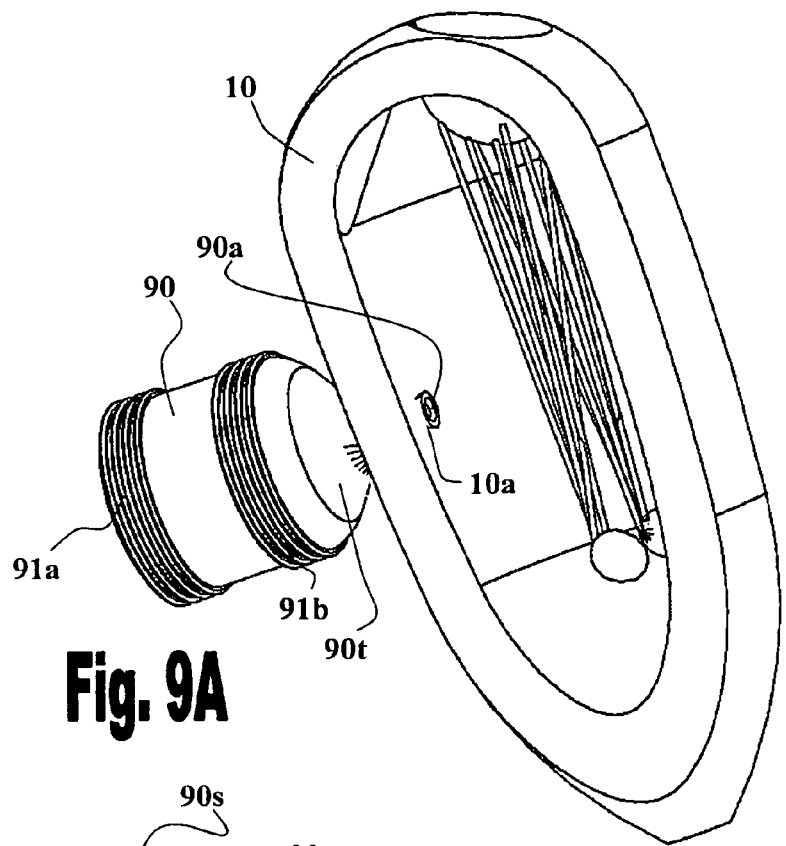
FIGS. 9A and 9B schematically illustrate a ventricular function assisting device employing an electromagnetically driven plunger.
Figure 9B:
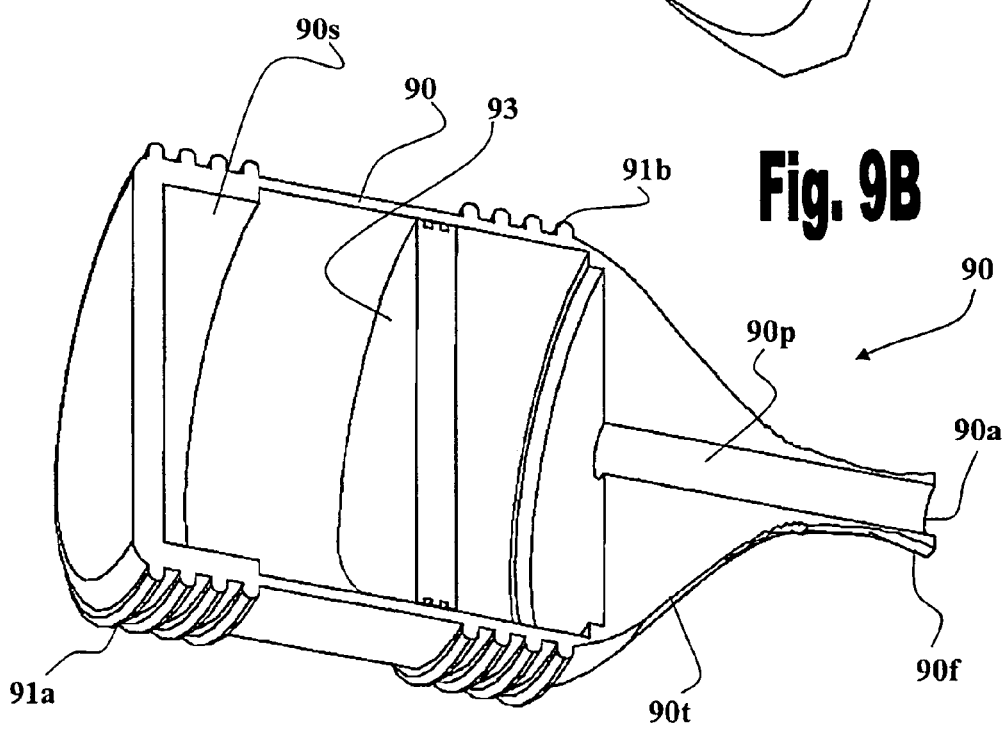

FIGS. 9A and 9B schematically illustrate a ventricular function assisting device 90 employing an electromagnetically driven plunger 93. Device 90 is preferably made from a hollow cylindrical body which interior may be accessed via bore 90p provided in its front wall 90t. Front wall 90t may be advantageously formed in a conical shape having a flare 90f at its tip for assisting in mounting it in the wall of heart 10. Said mounting of ventricular function assisting device 90 is preferably carried out by forming a small incision 10a in the wall of the heart and introducing the flaring front end 90f of device 90 thereinto such that the opening 90a of bore 90p communicates with an interior of a heart chamber. Device 90 may be secured in its mounted state to the heart 10 by means of pressure, tightening or suturing. Volumes of blood may thus be injected/discharged into/from device 90.

With reference to FIG. 9B, ventricular function assisting device 90 further comprises an electromagnetic plunger 93, and a first coil 91a, winded over (or inside) a rear section of cylindrical body of device 90, and a second coil 91b wound over (or inside) a front section of device 90 near its front wall 90t, said coils are adapted to receive electrical currents and apply opposing magnetic fields generally perpendicular to the plane of magnetic plunger 93, such that said electromagnets may be activated alternately to apply back and forth driving forces over magnetic plunger 93.

More particularly, during the diastole second coil 91b is activated to apply axial forces over plunger 93 for sliding it towards the rear side of device 90 (i.e., by applying magnetic repulsion forces) and thereby pump a volume of blood (e.g., about 10-200 ml) thereinto and assist in reducing the pressure in heart 10 and in pumping blood into it. The rearward movement of plunger 93 may be limited by a stopper 90s formed in, or attached on, a rear section of the internal wall of device 90. During the systole, the first coil 91a is activated to apply axial forces over plunger 93 for sliding it towards the front side of device 90 (i.e., by applying magnetic attraction forces) and thereby discharge a volume of blood therefrom and assist in increasing the pressure in heart 10 and in pumping blood therefrom.

Ventricular function assisting device 90 may be manufactured from a type of biocompatible metallic material, for example stainless steel, or alternatively from a type of biocompatible polimer, preferably from stainless steel, its diameter may generally be in the range of 10 to 60 mm, preferably about 25 mm, and its length may generally be in the range of 10 to 40 mm, preferably about 30 mm. The volume of device 90 may generally be in the range of 10 to 200 ml, preferably about 50 ml. Coils 91 are preferably made from an electrically conducting wire made from copper the diameter of the wires and the number of turns are preferably adjusted for generating a magnetic filed in the range of 0.000001 to 0.1 Tesla responsive to electrical currents in the range of 0.0001 to 10 amperes.

The electrical current may be supplied to coils 91 by an implantable battery (not shown). The operation of coils 91 may be activated by an implantable control logic and/or programmable controller (not shown), employing ECG sensing means (or pacemaker) for synchronizing device operation with the heart function.

Magnetic plunger 93 is a permanent magnet made from a type of magnetic material, such as for example stainless steel, its thickness may generally be in range of 0.5 to 3 mm, and its diameter is adjusted to allow it to smoothly slide inside device 90 along its length. The magnetic strength of magnetic plunger 93 may generally be in the range of 0.001 to 1000 gauss.

Ventricular function assisting device 90 may be connected to the heart in a minimal invasive procedure via a small opening formed in the patient's chest. The device may be connected to the tissue of the left ventricle by suturing, insertion under pressure and/or threading it into the tissue.

Device 12 may be installed on the wall of the heart of a patient in a procedure comprising the following steps: open chest surgery, thoracotomy, or minimal invasive thoracoscopy. Apertures 10a and 10b may be formed in the wall of heart 10 by a surgical cutting device or by a needle, and device 12 may be attached to the wall of the heart 10 by pressure, surgical sutures, stapling devices or adhesives.

Figure 10A:
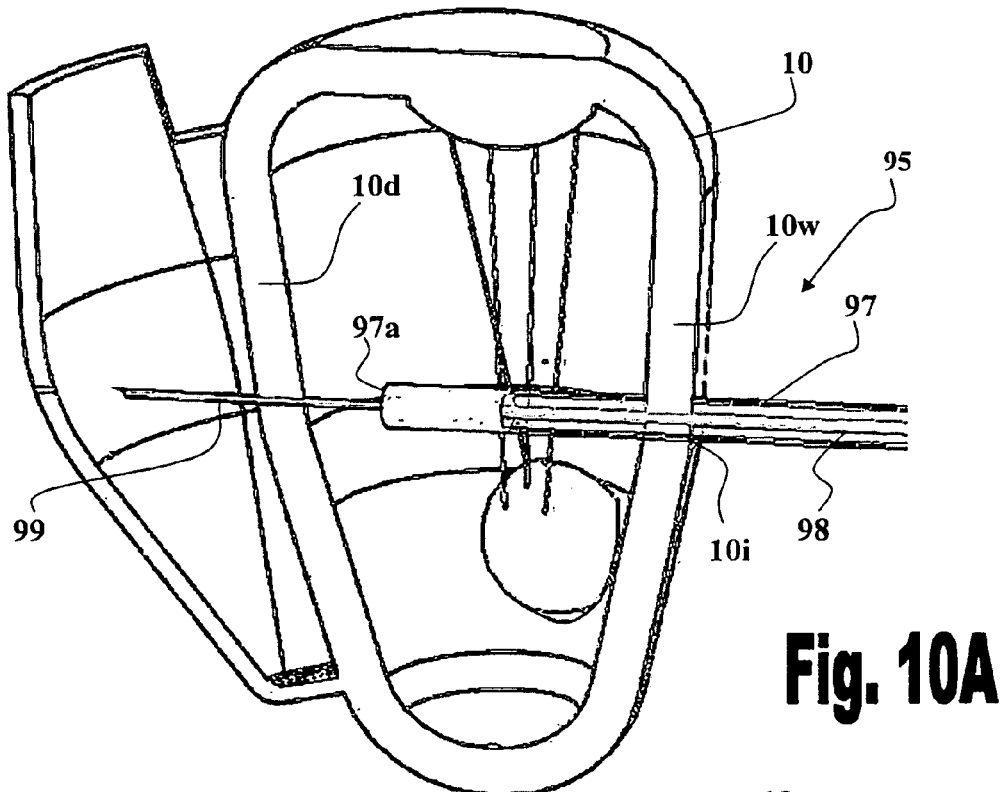
FIGS. 10A and 10B schematically illustrate a method and apparatus for inserting treatment devices into the heart and for mounting the same on its inner wall.
Figure 10B:
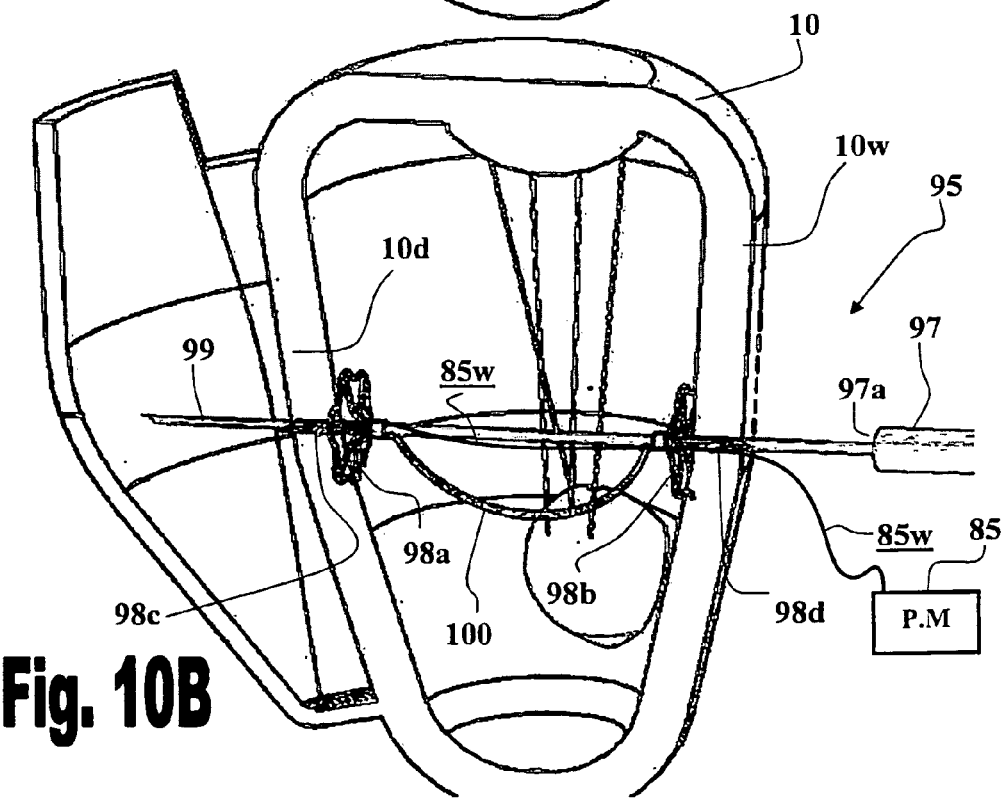

FIGS. 10A and 10B schematically illustrate a method and a device 95 for delivering treatment device 100 into the heart and for mounting the same on its inner wall. Treatment device 100 is configured for implantation inside a ventricle of a living heart 10, which includes fixation elements 98a and 98b configured to be pressed onto opposing walls regions in the ventricle by an elastic (spring-like) energy absorbing element (100). Fixation elements 98a and 98b (also referred to herein as expandable elements) are connected in both sides of the elastic elements which is designed to be inserted into the ventricle in a preloaded state. After implantation in the ventricle of heart 10 energy from the ventricular movement of the heart is absorbed in the elastic element, such that additional energy is absorbed by it during the systolic phase of the heart, which energy is then released to the ventricle through the fixation elements 98a and 98b during the diastolic phase, thereby assisting in improving diastolic functioning of the heart.

Delivery tool 95 generally comprises a tube 97 and a guide wire 99 passing there inside. At the first step of an insertion procedure the guide wire 99 is inserted at the desired location to mark the device implantation trajectory. The device 100 can be placed at different locations, e.g., between the lateral wall to the septum, or between the anterior to the posterior walls. Tube 97 is introduced into heart 10 over guide wire 99 via a small incision 10i formed in the free wall 10w of the heart 10, such that opening 97a of tube 97 is placed more or less in front of the distal wall 10d.

In this state a device 100 (e.g., bent spring) may be installed inside heart 10. The device to be installed is advanced through tube 97 and it may be installed by performing the following steps: advancing a portion of device 100 such that a first expandable element 98a of device 100 is released through opening 97a, the state of said first expandable element 98a is then changed into an open (deployed) state and pressed against the distal wall 10d of heart 10 by distal anchoring means 98c (e.g., bars, screw, hook); retracting tube proximally such that a second expandable element 98b is released via opening 97a, said second expandable element 98b is then changed into its deployed state and pressed against the proximal wall 10w of heart 10 by wall anchoring means 98d (e.g., bars, screw, hook) as tube 97 is withdrawn from heart 10 via incision 10i.

Tube 97 may be manufactured from Nylon, Silicon, Teflon, or any kind of suitable polymer, preferably from Teflon, and its diameter may generally be about 2 to 10 mm.

Device 100 may be used for applying forces over heart walls 10w and 10d by means of, but not limited to: buckling bar, torsion spring (not shown), or pressing spring (not shown).

Wall anchoring 98d and/or distal anchoring 98c may be used as electrical connecting means for delivering electrical signals produced by pacemaker 85. When pacemaker 85 is attached to the wall anchoring 98d and distal anchoring 98c that is implanted in the heart tissue and used to conduct the electric signal from pacemaker 85 via electrical cables 85w to heart tissue and to pace the left ventricle, or the right ventricle, or both of them.

Expandable elements 98a and 98b may be manufactured from an elastic material, preferably from nitinol, and it may be formed in a shape of a flower which leaves (e.g., having 3 to 12 leaves each having a length of about 3 to 20 mm) are configured to allow it to be packed compactly such that it may be delivered through tube 97 and open laterally when it is released therefrom. Expandable elements 98a and 98b may be manufactured form a thin and elastic wire having a diameter of about 0.1 to 2 mm.

Distal anchoring 98c and wall anchoring 98d may be manufactured from nitinol or Conichrome (fwm 1058), for example, in shape of short tubes having a length of about 3 to 20 mm and inner diameter of about 1 to 10 mm. Distal anchoring 98c and wall anchoring 98d are preferably connected to the centers of expandable elements 98a and 98b and perpendicular to their plains when in their deployed state, to allow them to be delivered over guide wire 99. Distal anchoring 98c and wall anchoring 98d are configured to be introduced into the wall of the heart for attaching treatment device 100. This is preferably achieved by screwing or sticking.

Pacemaker 85 can be implant together with device 100, or later if required, through tube 97. Pacemaker 85 is implanted in the patient's body in substantially the same way as in conventional pacemaker procedures, such that it may be placed under the chest or abdomen skin of the patient, but instead of using the conventional pacemaker electrodes the electrical signals it produces are delivered to the patient's heart through anchoring means the wall anchoring 98c and/or the distal anchoring 98d.

All of the above mentioned parameters are given by way of example only, and may be changed in accordance with the differing requirements of the various embodiments of the present invention. Thus, the abovementioned parameters should not be construed as limiting the scope of the present invention in any way. In addition, it is to be appreciated that the different plungers, tubes, springs, and other members, described hereinabove may be constructed in different shapes (e.g. having oval, square etc. form in plan view) and sizes differing from those exemplified in the preceding description.

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

The invention claimed is:

1. A ventricular function assisting apparatus comprising anchoring means capable of being attached to the wall of the heart, elastic elements capable of being attached to said anchoring means, at least two restrictive elements adapted to encircle a perimeter of the heart, said restrictive elements are capable of being changed between an engaging state and a non-engaging state over the heart, and elongated flexible elements capable of being attached between said restrictive elements via their extremities while being movably engaged in said anchoring means along portions of their lengths, wherein said elastic elements are capable of being elastically deformed and store potential energy in them during the systolic phase and release said stored energy during the diastolic phase and thereby apply radially outward and tangentially directed forces over the wall of the heart, wherein said ventricular function assisting device is capable of being selectively changed between two modes of operation by changing the state of said restrictive means between their non-engaging and engaging states over the heart, and wherein the elastic elements are made in a "V"-like shape having torsion loop(s) at their apexes and two side arms attached at one end to said torsion loop(s), and wherein each of said side arms comprises attachment components at their free ends capable of being received and held in the anchoring means.

2. Apparatus according to claim 1 wherein the attachment components are made in a "G"-like or "C"-like shape.

3. Apparatus according to claim 1 wherein the anchoring means are made from a turned wire having a bottom and top portions, wherein said bottom portion is formed in a helical shape adapted to be screwed into a soft tissue and its top portion comprises one or more retaining parts configured to receive the attachment components of the elastic elements.

4. Apparatus according to claim 3 wherein the retaining parts are made from a curved wire configured to receive and hold the attachment components of the elastic elements while allowing non-interlocking passage of the elongated flexible elements through it.

5. Apparatus according to claim 3 wherein the top portion of the anchoring means comprises a flanged rod having circumferential gaps formed between its flanges capable of receiving and holding the attachment components of the elastic elements and/or wherein the top portions of the anchoring means comprise a dome-like cover.

6. Apparatus according to claim 1 wherein the restrictive elements are made from a rigid, semi-rigid or flexible, circular stripe, or in a form of a flexible wavy configuration, wherein said restrictive elements comprise a fastening mechanism capable of changing its circumference from a non-engaging state into an engaging state by reducing its circumference.

7. Apparatus according to claim 6 wherein the fastening mechanism is implemented by means of a fastening screw, or by means of a spring and a removable support bar attached over a gap formed in the restrictive element.

8. Apparatus according to claim 1 wherein the flexible elongated elements are attached to the restrictive elements by means of pulling, or pushing, springs.

9. Apparatus according to claim 1 employing only one restrictive element, wherein the flexible elongated elements are attached at one end to said restrictive element while their other ends are attached together by a connecting component near the apex of the heart.

10. Apparatus according to claim 1 further comprising a pacemaker electrically coupled to one or more of the anchoring means for delivering electrical signals to the tissue of the heart.

11. A kit comprising elements of ventricular function assisting device according to any one of claim 1, fastening means capable of holding the top portion of the anchoring means, and a screwing tool comprising: a proximal handle having a rotatable wheel disposed in it; a hollow shaft attached to said handle, said hollow shaft comprises a rotatable rod mechanically linked to said rotatable wheel; a hinged head attached at the distal end of said hollow shaft in which there is a rotatable holder capable of receiving and holding said fastening means in it, wherein said rotatable rod and said rotatable holder are mechanically linked such that rotations of said wheel are delivered thereby to said rotatable holder.

12. A kit according to claim 11 wherein the screwing tool further comprises a foldable locator provided in its hinged head, said foldable locator is adapted for indicating the distance between adjacent anchoring means placed on the wall of the heart, thereby assisting in the positioning of the neighboring anchoring means.

13. The kit according to claim 11, further comprising a delivery tool having an elongated stack capable of holding a plurality of said anchoring means, said elongated stack comprising a pushing spring adapted to advance said anchoring means distally toward a distal opening wherein there is a screwing head mechanically linked to an electrical motor, wherein said screwing head is capable of holding the distalmost anchoring means in said stack, move it out of said stack via said distal opening and rotate it, thereby enabling its insertion into the tissue.

14. The kit according to claim 13, wherein the delivery tool further comprises optical guiding means mounted on opposing sides in a distal section of said delivery tool, said optical guiding means are adapted to emit a light beam capable of designating a new location for placing a new anchoring means, with reference to the neighboring previously-positioned anchoring means.

15. The kit according to claim 11 further comprising a delivery tool for delivering and attaching elastic elements to anchoring means attached to a tissue, said tool comprising a proximal handle having a slider element movably placed therein and capable of being moved between proximal and distal states, a slidable hollow shaft mechanically linked to said slider element, and an elongated rod fixedly attached to said proximal handle and passing inside said handle and said slidable hollow shaft, wherein said slider element can be changed between a proximal state and a distal state and correspondingly move slidable hollow shaft, and wherein said elongated rod comprises a retaining part adapted to receive and hold the torsion loop(s) of an elastic element when said slider element in said proximal state, such that the arms of said elastic elements are capable of being folded into said slidable hollow shaft by changing the sate of said slider element into said distal state.

16. A ventricular function assisting apparatus comprising anchoring means capable of being attached to the wall of the heart, elastic elements capable of being attached to said anchoring means, at least two restrictive elements adapted to encircle a perimeter of the heart, said restrictive elements are capable of being changed between an engaging state and a non-engaging state over the heart, and elongated flexible elements capable of being attached between said restrictive elements via their extremities while being movably engaged in said anchoring means along portions of their lengths, wherein said elastic elements are capable of being elastically deformed and store potential energy in them during the systolic phase and release said stored energy during the diastolic phase and thereby apply radially outward and tangentially directed forces over the wall of the heart, and wherein said ventricular function assisting device is capable of being selectively changed between two modes of operation by changing the state of said restrictive means between their non-engaging and engaging states over the heart, wherein the anchoring means are made from a turned wire having a bottom and top portions, wherein said bottom portion is formed in a helical shape adapted to be screwed into a soft tissue and its top portion comprises one or more retaining parts configured to receive the attachment components of the elastic elements, wherein the retaining parts are made from a curved wire configured to receive and hold the attachment components of the elastic elements while allowing non-interlocking passage of the elongated flexible elements through it.

* * * * *